United States Patent
Han et al.

(10) Patent No.: US 10,950,800 B2
(45) Date of Patent: Mar. 16, 2021

(54) COMPOUNDS FOR INFRARED LIGHT SENSING DEVICES, INFRARED LIGHT SENSING DEVICES, IMAGE SENSORS, AND ELECTRONIC DEVICES INCLUDING THE SAME

(71) Applicants: Samsung Electronics Co., Ltd., Suwon-si (KR); IMPERIAL INNOVATIONS LIMITED, London (GB)

(72) Inventors: Moon Gyu Han, Suwon-si (KR); Kyung Bae Park, Hwaseong-si (KR); Yong Wan Jin, Seoul (KR); Chul Joon Heo, Busan (KR); Brett Baatz, London (GB); Martin Heeney, London (GB); Minwon Suh, London (GB); Yang Han, London (GB); Ji-Seon Kim, London (GB)

(73) Assignees: Samsung Electronics Co., Ltd., Gyeonggi-do (KR); Imperial Innovations Limited, London (GB)

( * ) Notice: Subject to any disclaimer, the term of this patent is extended or adjusted under 35 U.S.C. 154(b) by 35 days.

(21) Appl. No.: 15/962,230

(22) Filed: Apr. 25, 2018

(65) Prior Publication Data
US 2018/0315933 A1   Nov. 1, 2018

(30) Foreign Application Priority Data
Apr. 26, 2017   (KR) .................. 10-2017-0053689

(51) Int. Cl.
| | | |
|---|---|---|
| *C07D 495/00* | (2006.01) | |
| *H01L 51/00* | (2006.01) | |
| *C07D 487/04* | (2006.01) | |
| *H01L 27/30* | (2006.01) | |
| *H01L 51/42* | (2006.01) | |
| *H01L 51/05* | (2006.01) | |

(52) U.S. Cl.
CPC ........ *H01L 51/0072* (2013.01); *C07D 487/04* (2013.01); *H01L 51/0065* (2013.01); *H01L 51/0068* (2013.01); *H01L 27/307* (2013.01); *H01L 51/055* (2013.01); *H01L 51/4253* (2013.01)

(58) Field of Classification Search
CPC . H01L 27/14; H01L 27/146; H01L 27/14649; H01L 27/28; H01L 27/30; C07D 495/00; C07D 495/02; C07D 495/04; C07D 495/14
See application file for complete search history.

(56) References Cited

U.S. PATENT DOCUMENTS

| | | | |
|---|---|---|---|
| 2013/0180589 A1* | 7/2013 | Yen .................. | C07D 495/04 136/263 |
| 2014/0252341 A1 | 9/2014 | Qiao et al. | |
| 2016/0035793 A1 | 2/2016 | Park et al. | |

FOREIGN PATENT DOCUMENTS

| | | | |
|---|---|---|---|
| JP | 2015065266 A | * | 4/2015 |
| KR | 20140072909 A | | 6/2014 |

OTHER PUBLICATIONS

Synthesis and Characterization of Quinoidal Diketopyrrolopyrrole Derivatives with Exceptionally High Electron Affinities, Ray et al., J. Phys. Chem. C 2017, 121, 16088-16097.*
Ambipolar organic field-effect transistors based on diketopyrrolopyrrole derivatives containing different π-conjugating spacers, Lin et al., J. Mater. Chem. C, 2016, 4, 4470-4477.*
Chao Wang et al., "Thiophene-Diketopyrrolopyrrole-Based Quinoidal Small Molecules as Solution-Processable and Air-Stable Organic Semiconductors: Tuning of the Length and Branching Position of the Alkyl Side Chain toward a High-Performance n-Channel Organic Field-Effect Transistor", "ACS Applied Materials & Interfaces", 2015, 7, pp. 15978-15987.
Christian Mayr et al., "Efficiency Enhancement of Organic Light-Emitting Diodes Incorporating a Highly Oriented Therrmally Activated Delayed Fluorescence Emitter", "Advanced Functional Materials", 2014, 24, pp. 5232-5239.
Chao Wang et al., "Thieno[3,2-b ] thiopene-Diketopyrrolopyrrole-Based Quindoidal Small Molecules: Synthesis, Characterization, Redox Behavior, and n-Channel Organic Field-Effect Transistors", "Chemistry—A European Journal", 2014, 20, pp. 13755-13761.
Zhengxu Cai et al., "Extended Conjugated Donor-Acceptor Molecules with E-(1,2-Difluorovinyl) and Diketopyrrolopyrrole (DPP) Moieties toward High-Performance Ambipolar Organic Semiconductors", "Chemistry—An Asian Journal", 2014, 9, pp. 1068-1075.
Jin-Dou Huang et al., "Electronic Structure and Microscopic Charge-Transport Properties of a New-Type Diketopyrrolopyrrole-Based Material", "Journal of Computational Chemistry", 2015, 36, pp. 695-706.
GuangYu Wang et al., "Theoretical study on the proporties of oligthiophene-diketopyrrolopyrrole dericatives: quinoidal versus aromatic", "Theoretical Chemistry Accounts", 2014, 133: 1453, pp. 1-8.

* cited by examiner

*Primary Examiner* — Haidung D Nguyen
(74) *Attorney, Agent, or Firm* — Harness, Dickey & Pierce, P.L.C.

(57) ABSTRACT

A compound for an infrared light sensing device may be represented by a particular chemical formula and may be included in an infrared light sensing device. An image sensor may include the infrared light sensing device, and an electronic device may include the image sensor.

14 Claims, 14 Drawing Sheets

COMPOUNDS FOR INFRARED LIGHT SENSING DEVICES, INFRARED LIGHT SENSING DEVICES, IMAGE SENSORS, AND ELECTRONIC DEVICES INCLUDING THE SAME

CROSS-REFERENCE TO RELATED APPLICATION

This application claims priority to and the benefit, under 35 U.S.C. § 119, of Korean Patent Application No. 10-2017-0053689 filed in the Korean Intellectual Property Office on Apr. 26, 2017, the entire contents of which are incorporated herein by reference.

BACKGROUND

1. Field

A compound for infrared light sensing devices, infrared light sensing devices, image sensors, and electronic devices including the same are disclosed.

2. Description of the Related Art

Recently, an attempt to research some example embodiments of a wireless communication, an infrared ray organic light emitting diode, a bio image sensor, and the like by using a material configured to absorb or emit light in a near infrared ray (NIR) region which has a longer wavelength than that of a visible light has been made. Particularly, an attention on importance of an infrared light absorption material and an infrared light sensing device using the same to improve low illumination sensitivity of an image sensor in a field of a night vision, an iris recognition, or the like has been paid.

An inorganic material such as silicon conventionally used as the infrared light absorption material may be configured to absorb remarkably small light in a near infrared region and may limit usage of a near infrared ray photo-sensing device.

Accordingly, development of an organic material having absorption characteristics regarding light in an infrared region as well as in a near infrared region has been made.

SUMMARY

Some example embodiments provide a compound for an infrared light sensing device, where the compound has absorption properties associated with light in an infrared region including a near infrared region, and the compound simultaneously has n-type semiconductor characteristics.

Some example embodiments provide an infrared light sensing device including a compound for an infrared light sensing device.

Some example embodiments provide an image sensor including an infrared light sensing device.

Still some example embodiments provide an electronic device including the image sensor.

According to some example embodiments, a composition for an infrared light sensing device may include a compound. The compound may be represented by Chemical Formula 1.

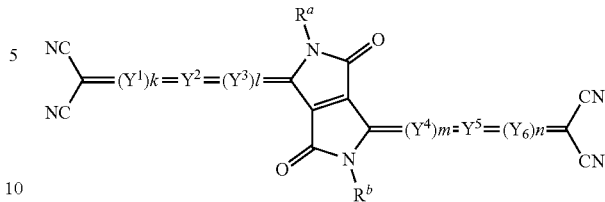

[Chemical Formula 1]

In Chemical Formula 1, $Y^1$ to $Y^6$ are independently a substituted or unsubstituted pentagonal ring including one of O, S, and Se or a fused ring of two or more substituted or unsubstituted pentagonal rings including one of O, S, and Se, k, l, m, and n are independently 0 or 1, and $R^a$ and $R^b$ are independently hydrogen or a monovalent organic group.

When k, l, m, and n are all 0, $Y^2$ and $Y^5$ may be independently a substituted or unsubstituted pentagonal ring including one of O, S, and Se, or a fused ring of two or more substituted or unsubstituted pentagonal rings including one of O, S, and Se.

In Chemical Formula 1, $R^a$ and $R^b$ may independently be hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a hydroxy group, a halogen atom, or a combination thereof.

In Chemical Formula 1, when k, l, m, and n are all 0, $Y^2$ and $Y^5$ may independently be represented by Chemical Formula 2 or 3.

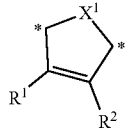

[Chemical Formula 2]

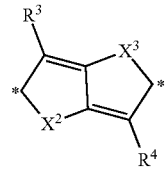

[Chemical Formula 3]

In Chemical Formulae 2 and 3, $X^1$ to $X^3$ are independently O or Se, $R^1$ to $R^4$ are independently hydrogen or a monovalent organic group, and

* is a linking point.

The compound for an infrared light sensing device may be represented by one of Chemical Formulae 4 to 7.

[Chemical Formula 4]

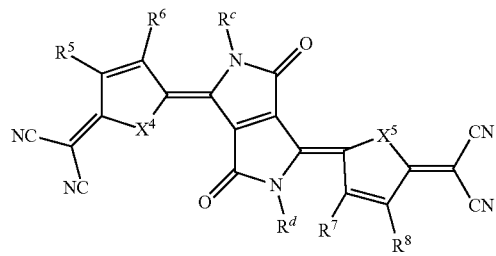

[Chemical Formula 5]

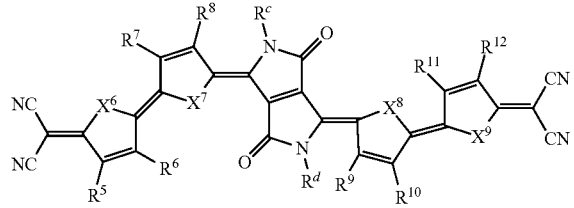

[Chemical Formula 6]

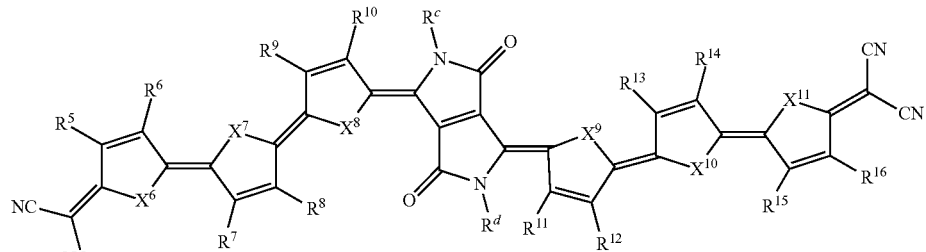

[Chemical Formula 7]

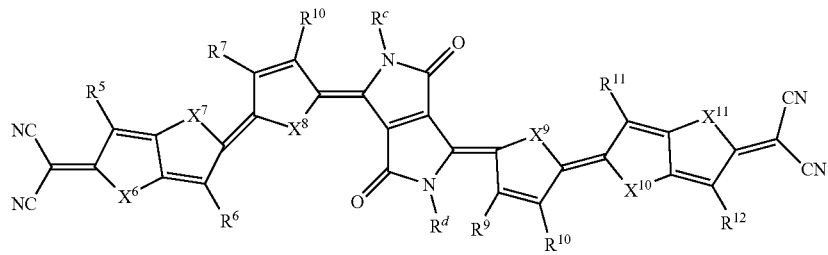

In Chemical Formulae 4 to 7, $X^4$ and $X^5$ are independently O or Se, $X^6$ to $X^{11}$ are independently one of O, S, and Se, $R^c$ and $R^d$ are independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a hydroxy group, a halogen atom, or a combination thereof, and $R^5$ to $R^{12}$ are independently hydrogen or a monovalent organic group.

The compound for an infrared light sensing device may be associated with a maximum absorption wavelength ($\lambda_{max}$) in a wavelength range of greater than or equal to about 700 nm and less than or equal to about 1,400 nm in a thin film state.

The compound for an infrared light sensing device may be an n-type semiconductor compound.

According to some example embodiments, an infrared light sensing device configured to sense light in an infrared wavelength region may include an upper electrode and a lower electrode facing each other and an infrared light absorption layer between the upper electrode and the lower electrode and including the compound for an infrared light sensing device represented by Chemical Formula 1.

According to some example embodiments, an image sensor includes the infrared light sensing device and a visible light sensing device including at least one of a blue photo-sensing device configured to sense light in a blue wavelength region, a red photo-sensing device configured to sense light in a red wavelength region, and a green photo-sensing device configured to sense light in a green wavelength region.

The blue wavelength region may be associated with a maximum absorption wavelength ($\lambda_{max}$) of greater than or equal to about 400 nm and less than 500 nm, the red wavelength region may be associated with a maximum absorption wavelength ($\lambda_{max}$) of greater than 580 nm and less than about 700 nm, the green wavelength region may be associated with a maximum absorption wavelength ($\lambda_{max}$) of about 500 nm to about 580 nm, and the infrared wavelength region may be associated with a maximum absorption wavelength ($\lambda_{max}$) of about 700 nm to about 1,400 nm.

The visible light sensing device and the infrared light sensing device may be stacked vertically.

The visible light sensing device and the infrared light sensing device may be in parallel horizontally.

According to some example embodiments, an electronic device includes the image sensor.

The electronic device may include a mobile phone, a digital camera, or a biometric camera.

The compound for an infrared light sensing device according to some example embodiments is an organic monomer, absorbs light in an infrared region including a near infrared region, and ensures charge mobility. Accordingly, an infrared light sensing device including the compound may realize high sensitivity and high luminance under a low illumination environment.

DETAILED DESCRIPTION

Figure 1:
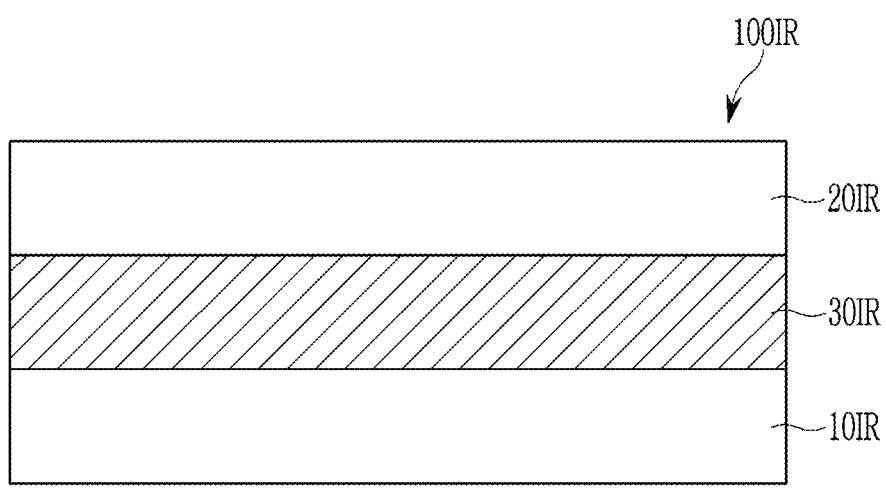
FIG. 1 is a cross-sectional view of an infrared light sensing device according to some example embodiments.

Hereinafter, example embodiments will be described in detail, and may be easily performed by a person having an ordinary skill in the related art. However, this disclosure may be embodied in many different forms and is not construed as limited to the example embodiments set forth herein.

As used herein, when a definition is not otherwise provided, "infrared light" refers to light in a wavelength region ("wavelength range," "range," etc.) of greater than or equal to about 700 nm and less than or equal to about 1,000 μm and "near-infrared light (NIR)" refers to a wavelength region of about 700 nm to about 2,500 nm within the range, and specifically a wavelength region of about 700 nm to about 1,400 nm.

As used herein, when a definition is not otherwise provided, "substituted" refers to replacement of a hydrogen atom of a compound or a functional group by a substituent selected from a halogen (F, Br, Cl, or I), a hydroxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid or a salt thereof, a C1 to C20 alkyl group, for example a C1 to C10 alkyl group, a C1 to C20 alkoxy group, for example a C1 to C10 alkoxy group, a C2 to C20 alkenyl group, a C2 to C20 alkynyl group, a C6 to C30 aryl group, a C7 to C30 arylalkyl group, a C3 to C20 heteroaryl group, a C3 to C20 heteroarylalkyl group, a C3 to C30 cycloalkyl group, a C3 to C15 cycloalkenyl group, a C6 to C15 cycloalkynyl group, a C2 to C20 heterocycloalkyl group, and a combination thereof.

In addition, "substituted" in an aromatic ring group refers to replacement of —CH$_2$— in the ring by —NR— (wherein R is selected from hydrogen, a halogen, a C1 to C10 alkyl group, a C1 to C10 alkoxy group, a C6 to C30 aryl group, and a C3 to C20 heteroaryl group), —O—, —S—, or —Se— or replacement of —CH= in the ring by —N=.

As used herein, when a definition is not otherwise provided, "hetero" refers to inclusion of one to three hetero atoms selected from N, O, S, P, and Si.

As used herein, when a definition is not otherwise provided, "halogen" refers to F, Br, Cl, or I.

Singular terms in the present specification may include a plurality of objects unless one object is precisely indicated.

All numerical ranges of the present specification include all numbers and ranges within set forth numerical ranges. In addition, numerical ranges and parameters indicating a broad scope of this disclosure are approximate values but the numerical values set forth in the Examples section are reported as precisely as possible. However, it should be understood that such numerical values inherently contain certain errors resulting from the measurement equipment and/or measurement technique.

According to some example embodiments, a composition for an infrared light sensing device may include a compound for an infrared light sensing device, where the compound is represented by Chemical Formula 1.

[Chemical Formula 1]

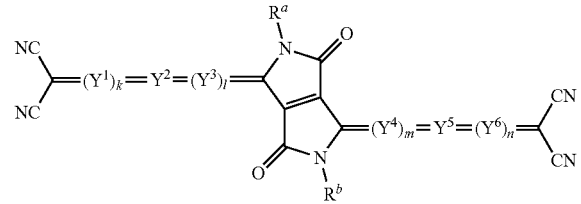

In Chemical Formula 1,

Y$^1$ to Y$^6$ are independently a substituted or unsubstituted pentagonal ring including one of O, S, and Se, or a fused ring of two or more substituted or unsubstituted pentagonal rings including one of O, S, and Se, k, l, m, and n are independently 0 or 1, and R$^a$ and R$^b$ are independently hydrogen or a monovalent organic group, wherein, when k, l, m, and n are all ("each") 0, Y$^2$ and Y$^5$ are independently a substituted or unsubstituted pentagonal ring including one of O, S, and Se, or a fused ring of two or more substituted or unsubstituted pentagonal rings including one of O, S, and Se.

The compound for an infrared light sensing device is an organic monomer having a quinoid structure, wherein specifically diketopyrrolopyrrole (DPP) is positioned in the core, pentagonal rings or fused rings formed through fusion of the pentagonal rings represented by Y$^1$ to Y$^6$ are linked with both sides of the core, and dicyanomethylene is positioned at both terminal ends of the compound.

The compound for an infrared light sensing device represented by Chemical Formula 1 has bipolar characteristics by including an electron donor moiety and an electron acceptor moiety in one molecule. For example, in Chemical Formula 1, the pentagonal ring represented by Y$^1$ to Y$^6$ or a fused ring of the pentagonal ring may be an electron donor moiety and a dicyanomethylene at the both terminal ends may be an electron acceptor moiety.

For example, the electron donor moiety may be a substituted or unsubstituted pentagonal ring including one of O, S, and Se or a fused ring of two or more substituted or unsubstituted pentagonal rings including one of O, S, and Se (i.e., in Chemical Formula 1, $Y^2$ and $Y^5$, k, l, m, and n are 0). Herein, the fused ring group may be for example a fused ring of two, three, four, or five substituted or unsubstituted pentagonal rings including one of O and Se.

For another example, the electron donor moiety may further include a cyclic group represented by $Y^1$, $Y^3$, $Y^4$, or $Y^6$ at both sides or one side of $Y^2$ and $Y^5$ in Chemical Formula 1. That is, the electron donor moiety may include two or more substituted or unsubstituted pentagonal rings including one of O, S, and Se, or fused rings of two or more substituted or unsubstituted pentagonal rings including one of O, S, and Se. Herein, the fused ring group may be for example a fused ring of two, three, four, or five substituted or unsubstituted pentagonal rings including one of O, S, and Se.

A maximum absorption wavelength and/or charge mobility may be controlled by the number of the cyclic group represented by $Y^1$, $Y^3$, $Y^4$, or $Y^6$ and kinds of heteroatoms therein.

In Chemical Formula 1, $R^a$ and $R^b$ may be for example independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a hydroxy group, a halogen atom, or a combination thereof. For non-limiting examples, $R^a$ and $R^b$ may independently be hydrogen, a substituted or unsubstituted C1 to C30 alkyl group, a substituted or unsubstituted C6 to C30 aryl group, or a combination thereof, but is not limited thereto.

For example, In Chemical Formula 1, when k, l, m, and n are all 0, $Y^2$ and $Y^5$ may independently be represented by Chemical Formula 2 or 3, but is not limited thereto.

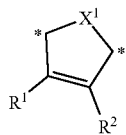

[Chemical Formula 2]

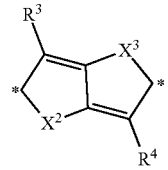

[Chemical Formula 3]

In Chemical Formulae 2 and 3,
$X^1$ to $X^3$ are independently O or Se,
$R^1$ to $R^4$ are independently hydrogen or a monovalent organic group, and
* is a linking point.

In Chemical Formulae 2 and 3, the monovalent organic group represented by $R^1$ to $R^4$ may be for example a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 heterocyclic group, a substituted or unsubstituted C2 to C30 alkenyl group, a substituted or unsubstituted C2 to C30 alkynyl group, a hydroxy group, a halogen atom, or a combination thereof, but is not limited thereto.

For example, the compound for an infrared light sensing device may be for example represented by one of Chemical Formulae 4 to 7, but is not limited thereto.

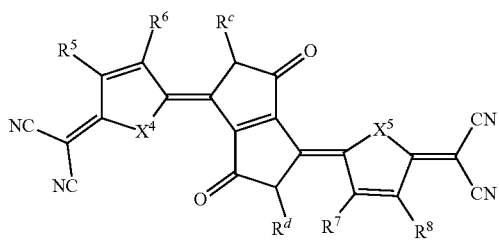

[Chemical Formula 4]

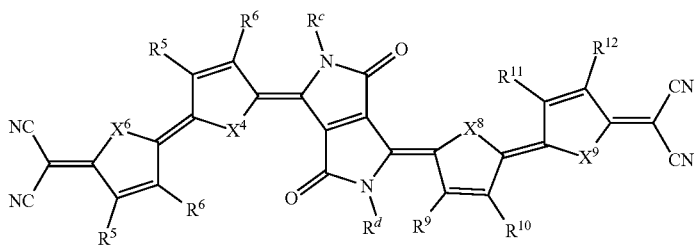

[Chemical Formula 5]

-continued

[Chemical Formula 6]

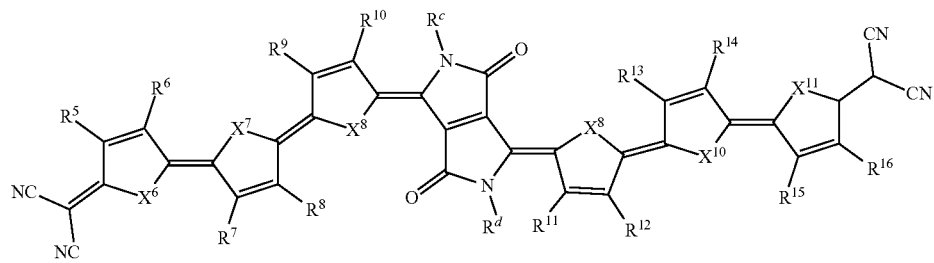

[Chemical Formula 7]

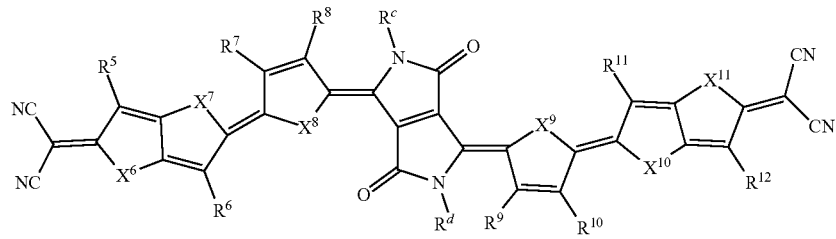

In Chemical Formulae 4 to 7, $X^4$ and $X^5$ are independently O or Se, $X^6$ to $X^{11}$ are independently one of O, S, and Se, $R^c$ and $R^d$ are independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a hydroxy group, a halogen atom, or a combination thereof, and $R^5$ to $R^{12}$ are independently hydrogen or a monovalent organic group.

Likewise, in Chemical Formulae 4 to 7, the monovalent organic group represented by $R^5$ to $R^{12}$ may be for example a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 heterocyclic group, a substituted or unsubstituted C2 to C30 alkenyl group, a substituted or unsubstituted C2 to C30 alkynyl group, a hydroxy group, a halogen atom, or a combination thereof, but is not limited thereto.

As described above, the compound for an infrared light sensing device may have a structure that each one pentagonal ring (or a fused pentagonal ring) is linked with diketopyrrolopyrrole (DPP) at both sides of the core, and the pentagonal ring (or fused pentagonal ring) contains O or Se in the structure. The compound for an infrared light sensing device may have a structure that a plurality of pentagonal ring (or fused pentagonal ring) is respectively linked with diketopyrrolopyrrole (DPP) at one side or both sides of the core, and herein, the pentagonal ring (or the fused pentagonal ring) contains O, S, or Se in the structure.

The compound has the above structure and thus may have absorption properties of light in an infrared region, particularly, in a near infrared region and simultaneously, secure charge mobility.

The compound for an infrared light sensing device may have ("may be associated with") a maximum absorption wavelength ($\lambda_{max}$) of ("in a wavelength range of") for example greater than or equal to about 700 nm and less than or equal to about 1,400 nm, greater than or equal to about 700 nm and less than or equal to about 1,300 nm, or greater than or equal to about 700 nm and less than or equal to about 1,000 nm and a full width at half maximum (FWHM) of greater than or equal to about 50 nm and less than or equal to about 150 nm, or greater than or equal to about 50 nm and less than or equal to about 130 nm in a thin film state.

The compound for an infrared light sensing device may have a molecular weight of about 300 to about 1,500, specifically about 350 to about 1,200, or more specifically about 400 to about 900. When the compound has a molecular weight within the ranges, crystallinity of the compound may be prevented and thermal decomposition of the compound by deposition during formation of a thin film may be effectively prevented.

For example, the compound may be an n-type semiconductor compound and may be configured to function as an n-type semiconductor and may be used as an n-type semiconductor when it has lower LUMO level than a p-type material used therewith.

An infrared light sensing device according to some example embodiments is described referring to drawings.

FIG. 1 is a cross-sectional view of an infrared light sensing device according to some example embodiments.

An infrared light sensing device 100IR includes a lower electrode 10IR and an upper electrode 20IR facing each other and an infrared light absorption layer 30IR between (e.g., "disposed between") the lower electrode 10IR and the upper electrode 20IR.

One of the lower electrode 10IR and the upper electrode 20IR may be an anode and the other may be a cathode. The lower electrode 10IR and the upper electrode 20IR may be all light-transmitting electrodes and may be for example made of a transparent conductor such as indium tin oxide (ITO) or indium zinc oxide (IZO) or may be a metal thin film having a thin thickness of several nanometers or several tens of nanometers or a metal thin film of a single layer or a multiple layer having a thin thickness of several nanometers to several tens of nanometers doped with a metal oxide.

The infrared light absorption layer 30IR may include the composition for an infrared light sensing device that includes the compound for an infrared light sensing device, where the compound is represented by Chemical Formula 1, as described above. The infrared light absorption layer 30IR may include the compound for an infrared light sensing device, where the compound is represented by Chemical Formula 1, as described above. The infrared light absorption layer 30IR may include p-type and n-type semiconductors and the compound for an infrared light sensing device represented by Chemical Formula 1 may be an n-type semiconductor. The compound for an infrared light sensing device represented by Chemical Formula 1 is mixed with various p-type semiconductor materials to form a pn junction and provide a bulk heterojunction (BHJ).

For example, the infrared light absorption layer 30IR may further include a quinoid metal complex compound, a cyanone compound, an immonium compound, a diimmonium compound, a triarylmethane compound, a dipyrromethene compound, a diquinone compound, a naphthoquinone compound, an anthraquinone compound, a squarylium compound, a ryleme compound, a phthalocyanine compound, a naphthalocyanine compound, a perylene compound, an anthraquinone compound, a nickel-dithiol complex, a derivative thereof or a combination thereof in addition to the compound for an infrared light sensing device represented by Chemical Formula 1, but is not limited thereto.

The infrared light absorption layer 30IR may have a thickness of about 1 nm to about 500 nm. Within the range, the thickness may be about 5 nm to about 500 nm, about 10 nm to about 500 nm, or about 30 nm to about 300 nm. Within the thickness ranges, light in an infrared region may be effectively absorbed, holes and electrons are effectively separated and transferred, and thereby photoelectric conversion efficiency may be effectively improved.

When light enters from the upper electrode 20IR, the infrared light absorption layer 30IR of the infrared light sensing device 100IR selectively absorbs (e.g., "is configured to selectively absorb") light in an infrared ray wavelength region and generates excitons therein. The excitons are separated into holes and electrons in the infrared light absorption layer 30IR, the separated holes are transferred to an anode which is one of the lower electrode 10IR and the upper electrode 20IR and the separated electrons are transferred into a cathode which is one of the lower electrode 10IR and the upper electrode, so as to flow a current. The separated electrons or holes may be collected in a charge storage (not shown).

The infrared light sensing device 100IR may selectively absorb light in an infrared region and may pass light in the wavelength region except the infrared region.

According to some example embodiments, an image sensor includes the infrared light sensing device.

Figure 2:
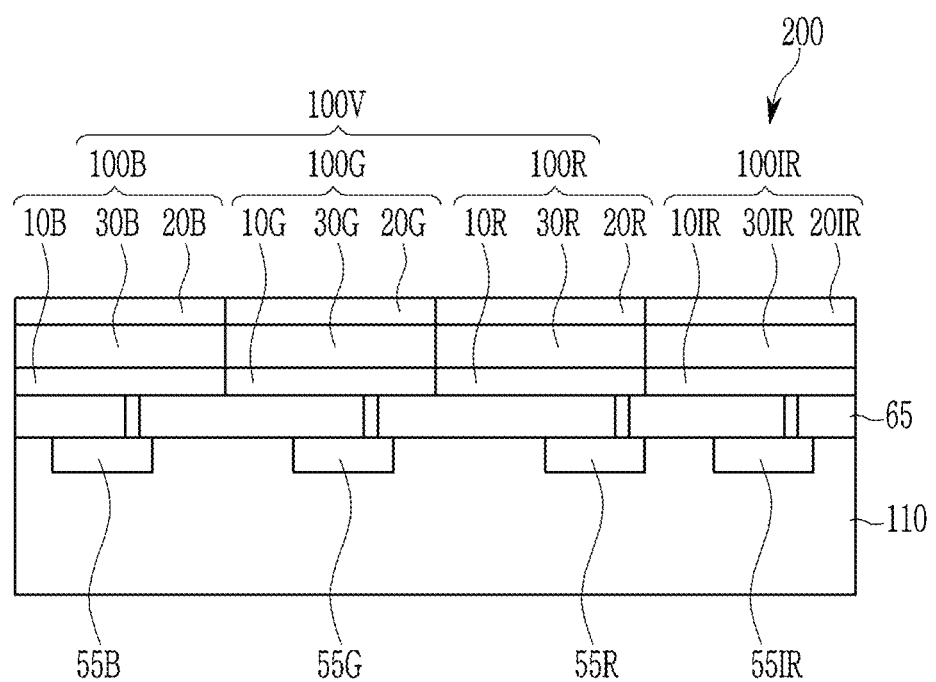
FIG. 2 is a schematic cross-sectional view of an image sensor according to some example embodiments.

FIG. 2 is a schematic cross-sectional view of an infrared cut filter according to some example embodiments.

Figure 3:
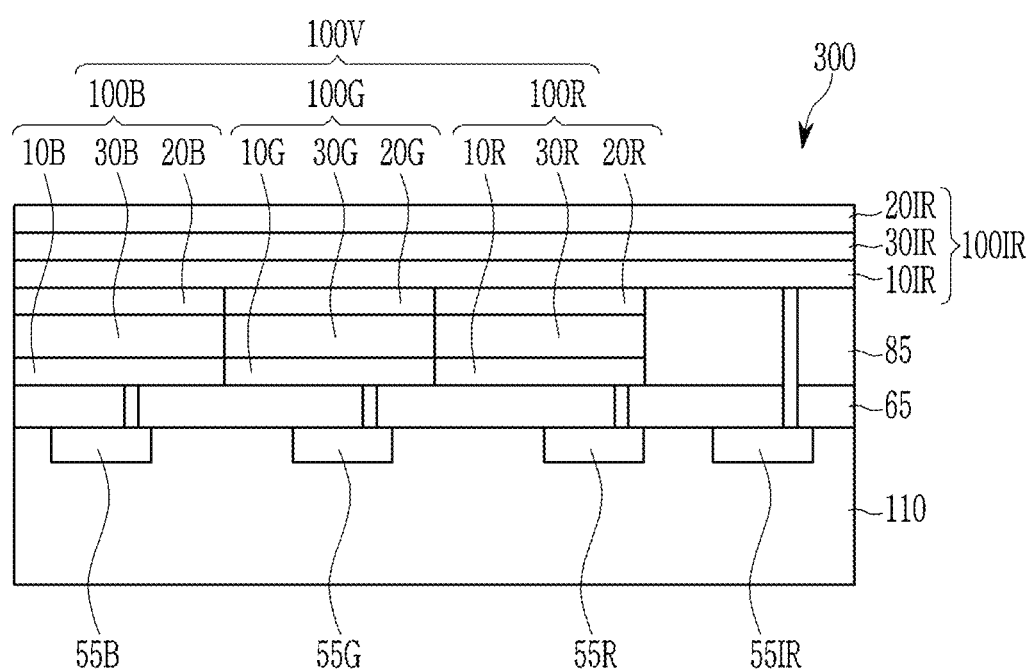
FIG. 3 is a schematic cross-sectional view of an image sensor according to some example embodiments.
Figure 4:
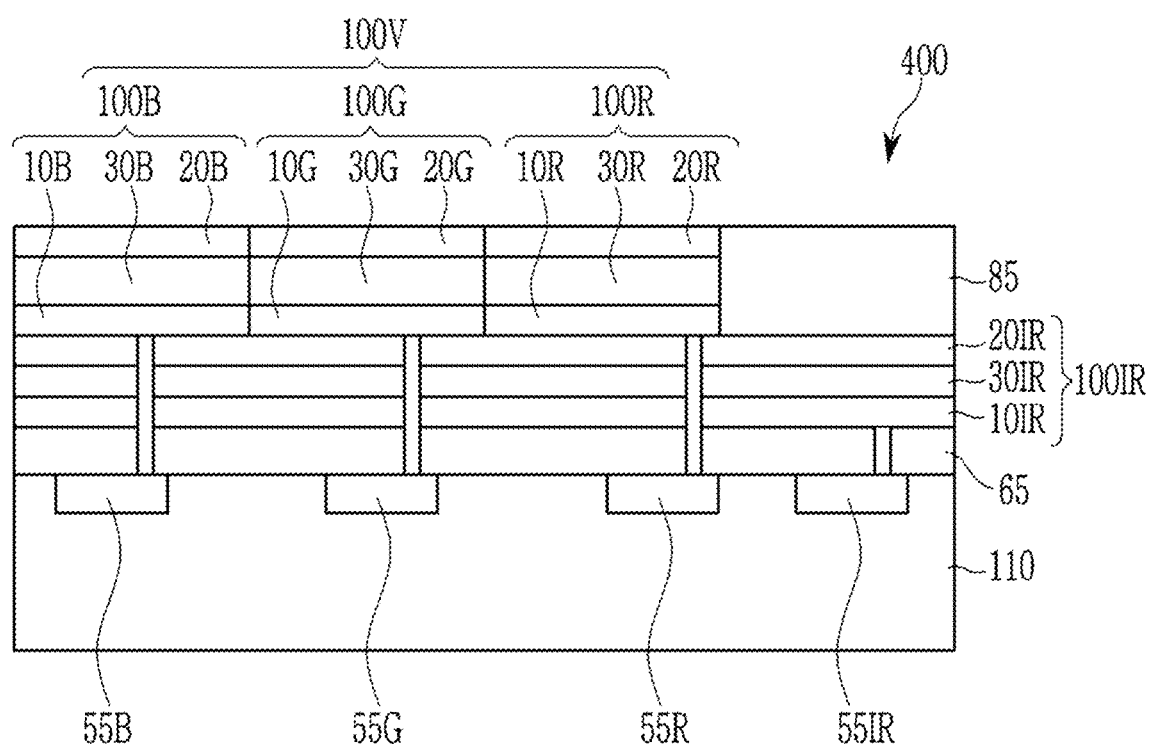
FIG. 4 is a schematic cross-sectional view of an image sensor according to some example embodiments.

Referring to FIG. 2, an image sensor 200 includes a semiconductor substrate 110 integrated with an infrared light charge storage 55IR, a blue charge storage 55B, a green charge storage 55G, a red charge storage 55R and a transmission transistor (not shown), a lower insulation layer 65, a blue photo-sensing device 100B, a green photo-sensing device 100G, a red photo-sensing device 100R, and an infrared light sensing device 100IR. As described herein, and as shown in FIGS. 2-4, at least one of the blue photo-sensing device 100B, the green photo-sensing device 100G, and the red photo-sensing device 100R may at least partially comprise a visible light sensing device 100V. As referred to herein, a light sensing device may be referred to interchangeably as a "photo-sensing device." For example, infrared light sensing device 100IR may also be referred to as an "infrared photo-sensing device," and visible light sensing device 100V may also be referred to as a "visible photo-sensing device."

The blue photo-sensing device 100B is configured to absorb ("sense") light in a blue wavelength region, the green photo-sensing device 100G is configured to absorb ("sense") light in a green wavelength region, and the red photo-sensing device 100R is configured to absorb ("sense") light in a red wavelength region. The infrared light sensing device 100IR may be configured to absorb ("sense") light in an infrared region ("infrared wavelength region").

For example, the blue wavelength region may have ("may be associated with") a maximum absorption wavelength ($\lambda_{max}$) of greater than or equal to about 400 nm and less than about 500 nm, the red wavelength region may have a maximum absorption wavelength ($\lambda_{max}$) of greater than about 580 nm and less than about 700 nm, the green wavelength region may have a maximum absorption wavelength ($\lambda_{max}$) of about 500 nm to about 580 nm, and the infrared region may have a maximum absorption wavelength ($\lambda_{max}$) of about 700 nm to about 1,400 nm.

The semiconductor substrate 110 may be a silicon substrate and may be integrated with the infrared light charge storage 55IR, the blue charge storage 55B, the green charge storage 55G, the red charge storage 55R, and the transmission transistor (not shown). The blue charge storage 55B, the green charge storage 55G, and the red charge storage 55R may be respectively integrated in each of a blue pixel, a green pixel, and a red pixel.

Charges absorbed in the infrared light sensing device 100IR, the blue photo-sensing device 100B, the green photo-sensing device 100G, and the red photo-sensing device 100R are collected in the infrared light charge storage 55IR, the blue charge storage 55B, the green charge storage 55G, and the red charge storage 55R which are electrically connected to each of the infrared light sensing device 100IR, the blue photo-sensing device 100B, the green photo-sensing device 100G, and the red photo-sensing device 100R.

Metal wires (not shown) and pads (not shown) are formed on the semiconductor substrate 110. In order to decrease signal delay, the metal wires and pads may be made of a metal having low resistivity, for example, aluminum (Al), copper (Cu), silver (Ag), and alloys thereof, but are not limited thereto.

The lower insulation layer 65 may be formed on the metal wires and pads. The lower insulation layer 65 may be made of an inorganic insulation material such as a silicon oxide and/or a silicon nitride, or a low dielectric constant (low K) material such as SiC, SiCOH, SiCO, and SiOF.

The blue photo-sensing device 100B, the green photo-sensing device 100G, the red photo-sensing device 100R, and the infrared photo-sensing device 100IR are formed on the lower insulation layer 65. The blue photo-sensing device 100B includes a lower electrode 10B, an upper electrode 20B, and a photoactive layer 30B selectively absorbing light in a blue wavelength region, the green photo-sensing device 100G includes a lower electrode 10G, an upper electrode 20G, and a photoactive layer 30G selectively absorbing light in a green wavelength region, the red photo-sensing device 100R includes a lower electrode 10R, an upper electrode 20R, and a photoactive layer 30R selectively absorbing light in a red wavelength region, and the infrared light sensing device 100IR includes a lower electrode 10IR, an upper electrode 20IR, and an infrared light absorption layer (or a photoactive layer) 30IR selectively absorbing light in an infrared light wavelength region.

The lower electrodes 10B, 10G, 10R, and 10IR and the upper electrodes 20B, 20G, 20R, and 20IR may be light-transmitting electrodes and may be made of, for example, a transparent conductor such as indium tin oxide (ITO), indium zinc oxide (IZO), zinc oxide (ZnO), tin oxide (SnO), aluminum tin oxide (AlTO), and fluorine-doped tin oxide (FTO), or may be a metal thin film having a thin thickness of several nanometers or several tens of nanometers or a metal thin film having a thin thickness of several nanometers to several tens of nanometers doped with a metal oxide.

The photoactive layers 30B, 30G, 30R, and 30IR may include a p-type semiconductor material and an n-type semiconductor material. The photoactive layer 30B of the blue photo-sensing device 100B may include a p-type semiconductor material selectively absorbing light in a blue wavelength region and an n-type semiconductor material selectively absorbing light in a blue wavelength region, the photoactive layer 30G of the green photo-sensing device 100G may include a p-type semiconductor material selectively absorbing light in a green wavelength region and an n-type semiconductor material selectively absorbing light in a green wavelength region, the photoactive layer 30R of the red photo-sensing device 100R may include a p-type semiconductor material selectively absorbing light in a red wavelength region and an n-type semiconductor material selectively absorbing light in a red wavelength region, and the photoactive layer 30IR of the infrared light sensing device 100IR may include a p-type semiconductor material selectively absorbing light in an infrared region ("infrared wavelength region") and an n-type semiconductor material selectively absorbing light in an infrared region.

The infrared light absorption layer (or the photoactive layer) 30IR of the infrared light sensing device 100IR may include the compound for an infrared light sensing device of Chemical Formula 1 as an n-type semiconductor material and a p-type semiconductor may be selected considering an energy level of the compound.

The infrared light sensing device 100IR may selectively absorb light in an infrared ray (i.e., near infrared ray) region of greater than or equal to about 700 nm and less than or equal to about 1,400 nm, greater than or equal to about 700 nm and less than or equal to about 1,300 nm, or greater than or equal to about 700 nm and less than or equal to about 1,000 nm.

FIG. 3 is a schematic cross-sectional view of an image sensor 300 according to some example embodiments. FIG. 4 is a schematic cross-sectional view of an image sensor 400 according to some example embodiments.

As shown in FIG. 2, the visible light sensing device 100V and the infrared light sensing device 100IR may be in parallel horizontally (may be disposed in parallel horizontally). As shown in FIGS. 3-4, the visible light sensing device 100V and the infrared light sensing device 100IR may be stacked vertically. Referring to FIG. 3, an image sensor 300 includes a semiconductor substrate 110 integrated with an infrared light charge storage 55IR, a blue charge storage 55B, a green charge storage 55G, a red charge storage 55R, and a transmission transistor (not shown), a lower insulation layer 65, an upper insulation layer 85, a blue photo-sensing device 100B, a green photo-sensing device 100G, a red photo-sensing device 100R, and an infrared light sensing device 100IR. The infrared light sensing device 100IR is formed on the entire surface of the blue photo-sensing device 100B, the green photo-sensing device 100G, the red photo-sensing device 100R. Other structures are the same as the image sensor of FIG. 2.

In the structure of FIG. 3, the infrared light sensing device 100IR is disposed on the lower insulation layer 65 and the blue photo-sensing device 100B, the green photo-sensing device 100G, and the red photo-sensing device 100R may be disposed thereon. An image sensor having such a structure is shown in FIG. 4.

The infrared light sensing device 100IR may selectively absorb light in an infrared ray (i.e., near infrared ray) region of greater than or equal to about 700 nm and less than or equal to about 1,400 nm, greater than or equal to about 700 nm and less than or equal to about 1,300 nm, or greater than or equal to about 700 nm and less than or equal to about 1,000 nm.

Figure 5:
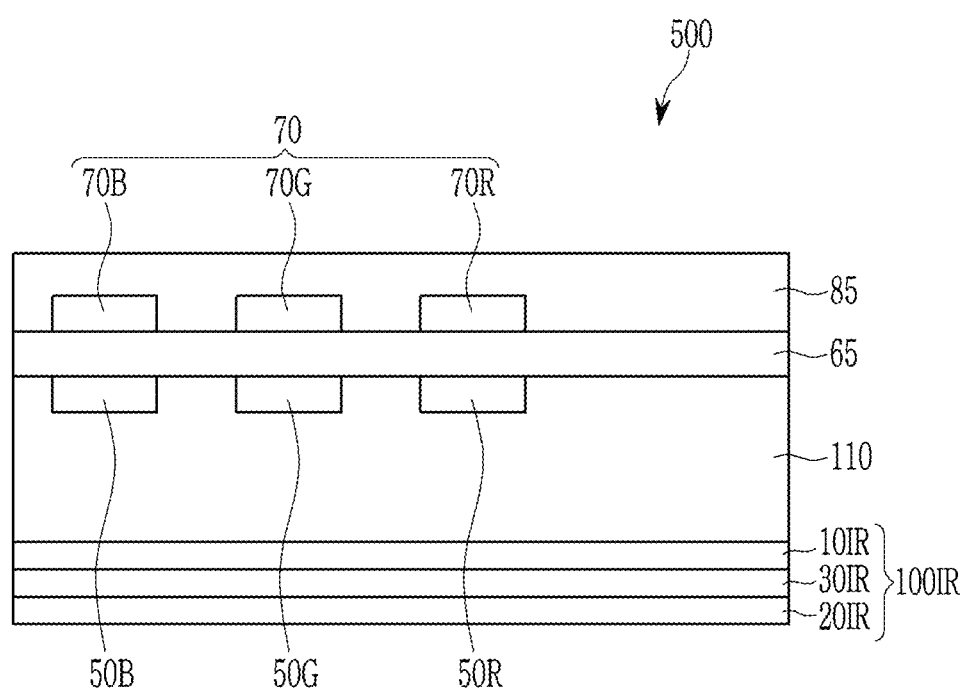
FIG. 5 is a schematic cross-sectional view of an image sensor according to some example embodiments.

FIG. 5 is a schematic cross-sectional view of an image sensor according to some example embodiment.

Referring to FIG. 5, an image sensor 500 includes a semiconductor substrate 110 integrated with a blue charge storage 55B, a green charge storage 55G, a red charge storage 55R, and a transmission transistor (not shown); a lower insulation layer 65, a color filter layer 70 and a upper insulation layer 85 on the semiconductor substrate 110; and an infrared/near infrared photo-sensing device 100IR under the semiconductor substrate 110.

Figure 6:
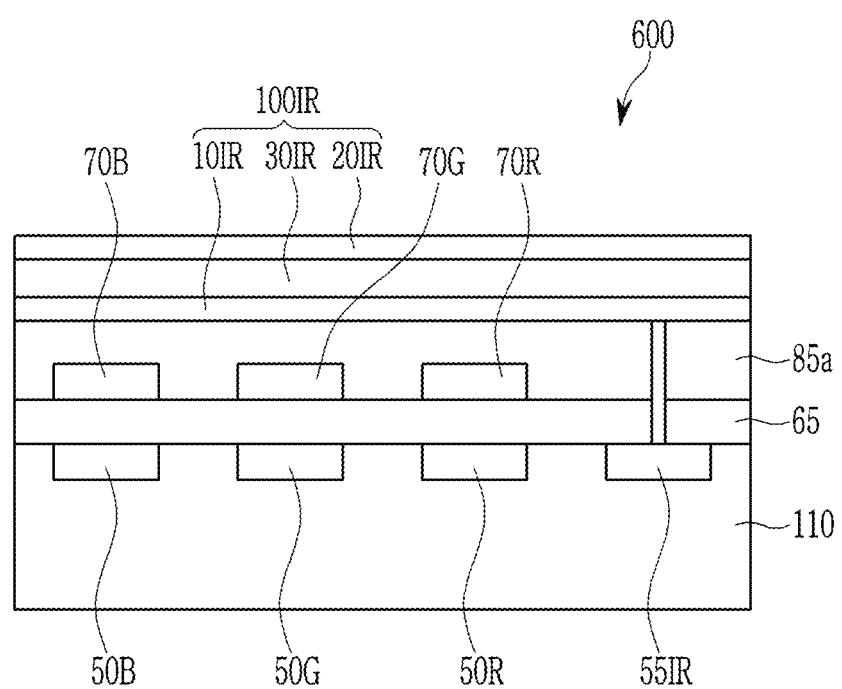
FIG. 6 is a schematic cross-sectional view of an image sensor according to some example embodiments.

FIG. 6 is a schematic cross-sectional view of an image sensor according to some example embodiment.

Referring to FIG. 6, an image sensor 600 includes a semiconductor substrate 110 integrated with a blue photo-diode 50B, a red photodiode 50R, a green photodiode 50G, an infrared light/near infrared light charge storage 55IR, and a transmission transistor (not shown); a lower insulation layer 65; a blue filter 70B; a green filter 70G; a red filter 70R; a upper insulation layer 85a; and an infrared/near infrared photo-sensing device 100IR.

Figure 7:
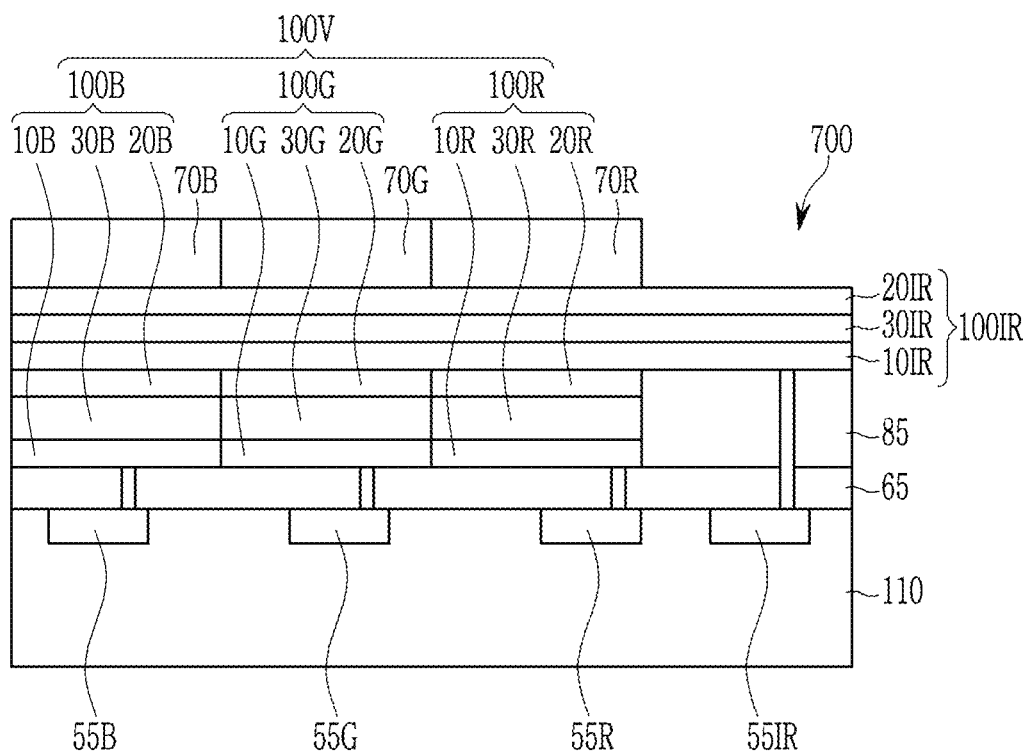
FIG. 7 is a schematic cross-sectional view of an image sensor according to some example embodiments.

FIG. 7 is a schematic cross-sectional view of an image sensor according to some example embodiment.

Referring to FIG. 7, an image sensor 700 includes a semiconductor substrate 110 integrated with an infrared light/near infrared light charge storage 55IR, a blue storage 55B, a green storage 55G, a red storage 55R and a transmission transistor (not shown); a lower insulation layer 65; a blue photo-sensing device 100B, a green photo-sensing device 100G, a red photo-sensing device 100R, an infrared/near infrared photo-sensing device 100IR, a blue filter 70B, a green filter 70G, and a red filter 70R.

Figure 8:
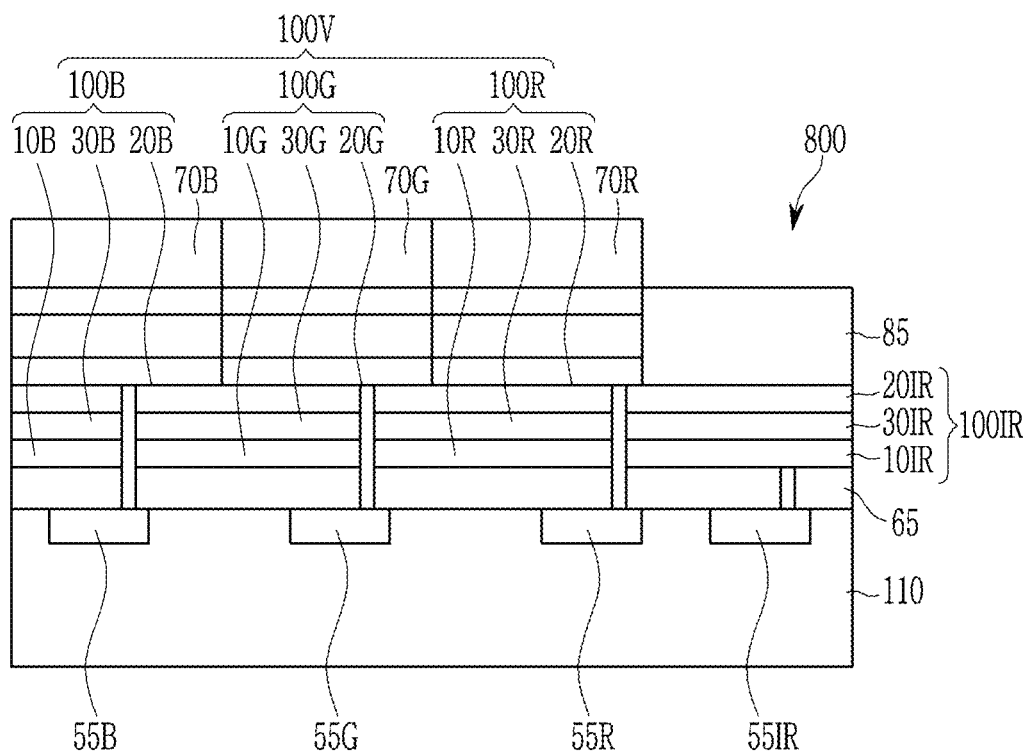
FIG. 8 is a schematic cross-sectional view of an image sensor according to some example embodiments.

FIG. 8 is a schematic cross-sectional view of an image sensor according to some example embodiment.

Referring to FIG. 8, an image sensor 800 includes a semiconductor substrate 110 integrated with an infrared light/near infrared light charge storage 55IR, a blue storage 55B, a green storage 55G, a red storage 55R and a transmission transistor (not shown); a lower insulation layer 65; a blue photo-sensing device 100B, a green photo-sensing device 100G, a red photo-sensing device 100R, an infrared/near infrared photo-sensing device 100IR, a blue filter 70B, a green filter 70G, and a red filter 70R.

Figure 9:
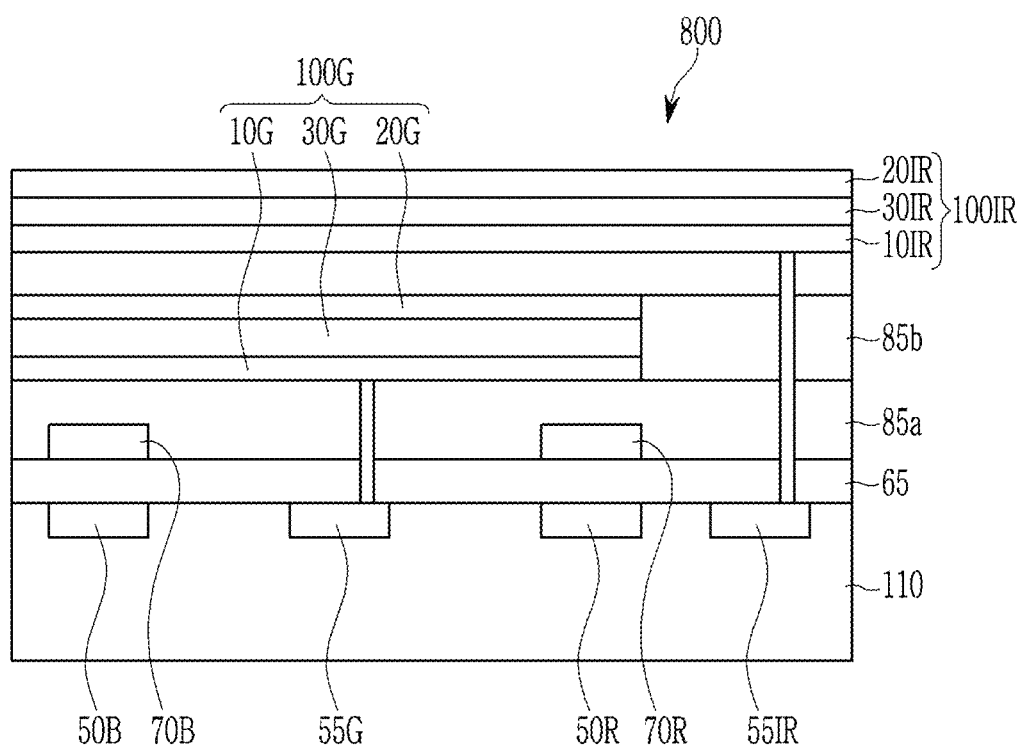
FIG. 9 is a schematic cross-sectional view of an image sensor according to some example embodiments.

FIG. 9 is a schematic cross-sectional view of an image sensor according to some example embodiment.

Referring to FIG. 9, an image sensor 800 includes a semiconductor substrate 110 integrated with an infrared light/near infrared light charge storage 55IR, a blue storage 55B, a green storage 55G, a red storage 55R and a transmission transistor (not shown); a lower insulation layer 65; a blue filter 70B; a red filter 70R; a upper insulation layers 85a and 85b; a green photo-sensing device 100G; and an infrared/near infrared photo-sensing device 100IR.

Figure 10:
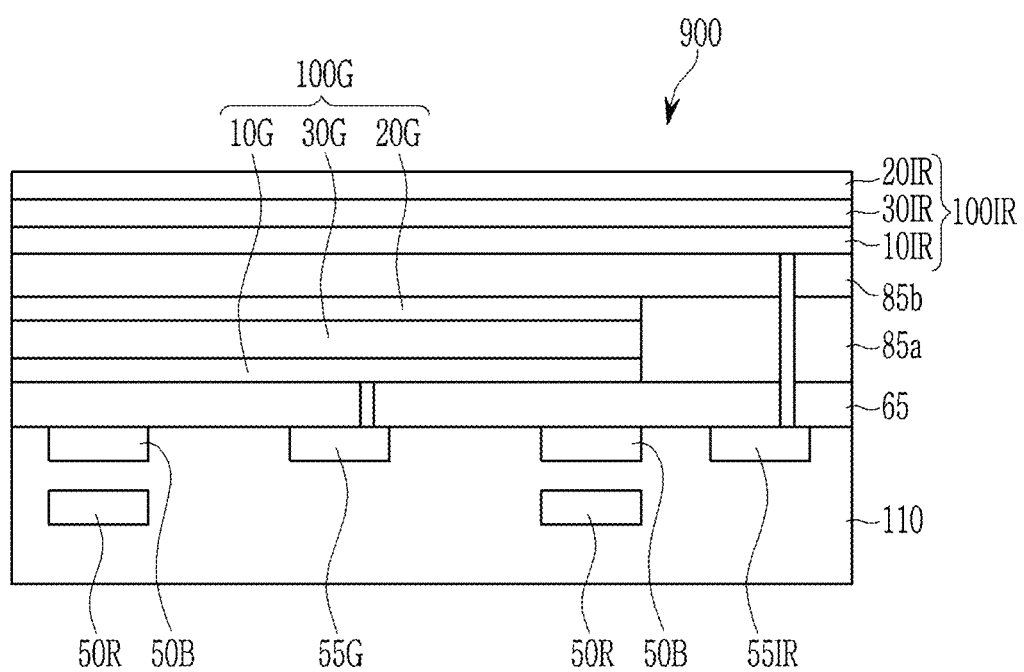
FIG. 10 is a schematic cross-sectional view of an image sensor according to some example embodiments.

FIG. 10 is a schematic cross-sectional view of an image sensor according to some example embodiment.

In the image sensor 900 of FIG. 10, the blue photodiode 50B and the red photodiode 50R are stacked perpendicularly, differing from the image sensor 800 of FIG. 9.

Figure 11:
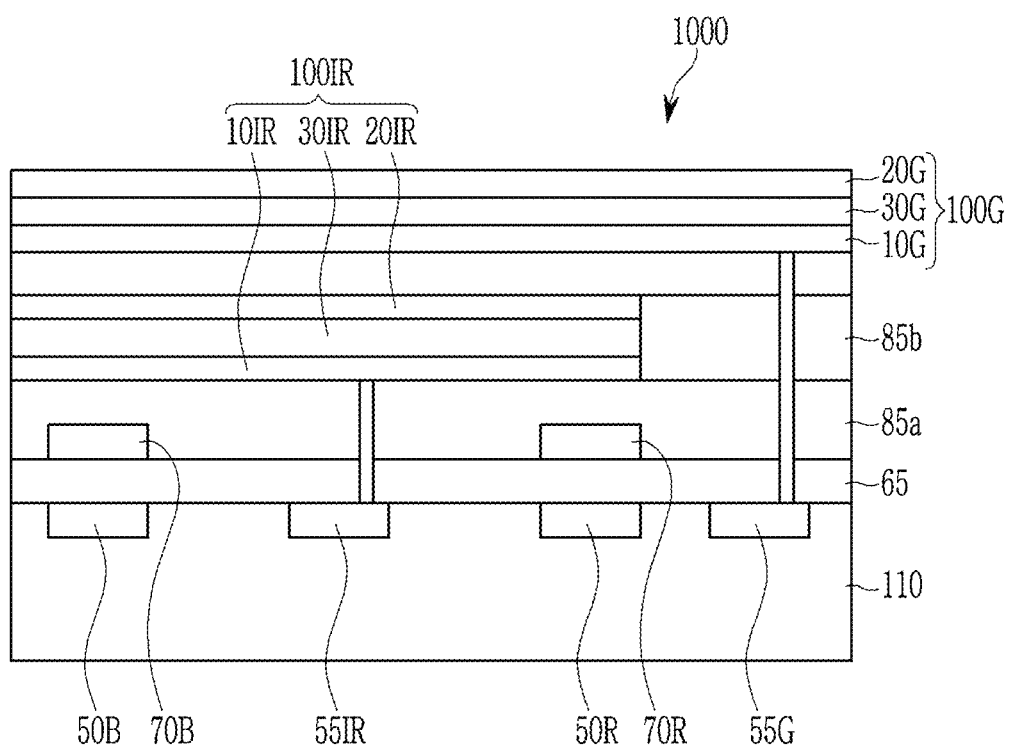
FIG. 11 is a schematic cross-sectional view of an image sensor according to some example embodiments.

FIG. 11 is a schematic cross-sectional view of an image sensor according to some example embodiment.

Referring to FIG. 11, an image sensor 1000 includes a semiconductor substrate 110 integrated with an infrared light/near infrared light charge storage 55IR, a blue storage 55B, a green storage 55G, a red storage 55R and a transmission transistor (not shown); a lower insulation layer 65; a blue filter 70B; a red filter 70R; a upper insulation layers 85a and 85b; an infrared/near infrared photo-sensing device 100IR; and a green photo-sensing device 100G.

Figure 12:
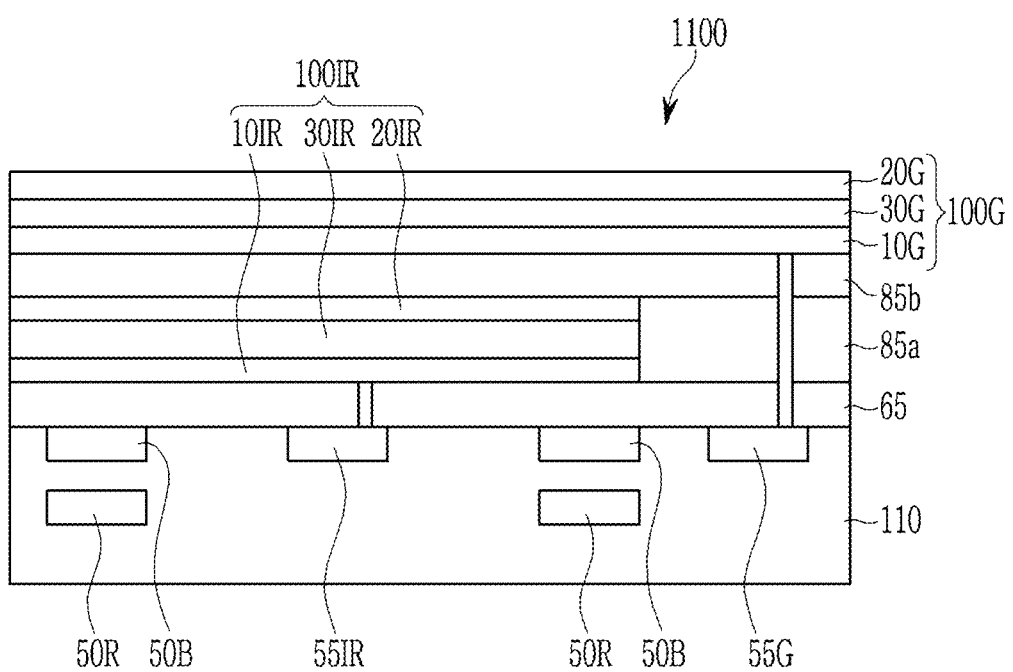
FIG. 12 is a schematic cross-sectional view of an image sensor according to some example embodiments.

FIG. 12 is a schematic cross-sectional view of an image sensor according to some example embodiment.

In the image sensor 1100 of FIG. 12, the blue photodiode 50B and the red photodiode 50R are stacked perpendicularly, differing from the image sensor 1000 of FIG. 11.

The image sensor may be applied to various electronic devices, for example, a mobile phone, a digital camera, and the like but is not limited thereto.

Figure 13:
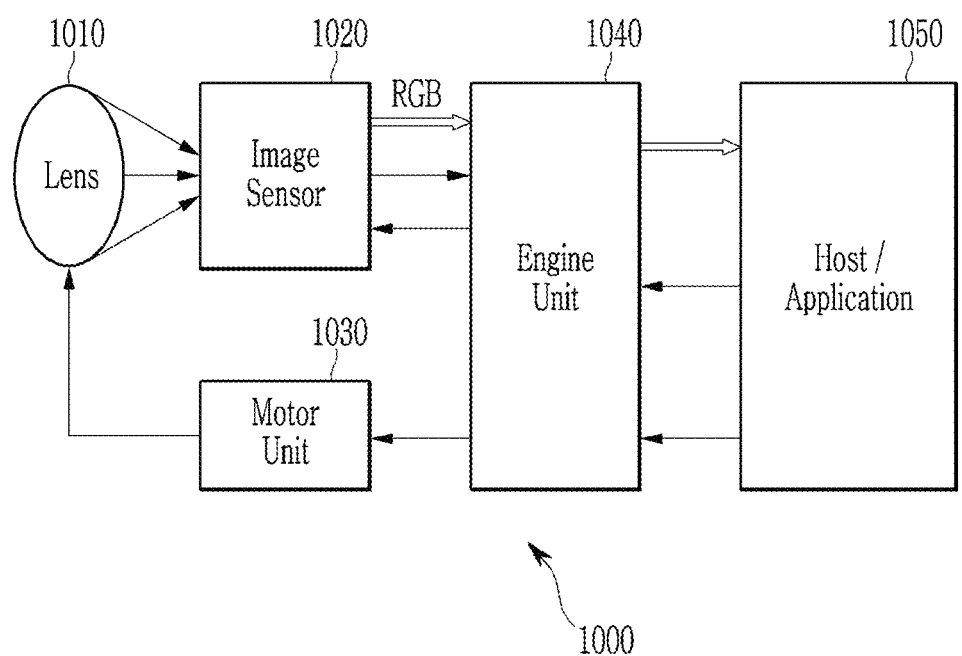
FIG. 13 is a block diagram of a digital camera including an image sensor according to some example embodiments.

FIG. 13 is a block diagram of a digital camera including an image sensor according to some example embodiments.

Referring to FIG. 13, a digital camera 1000 includes a lens 1010, an image sensor 1020, a motor unit 1030 ("motor apparatus"), and an engine unit 1040 ("engine apparatus"). The image sensor 1020 may be an image sensor according to any of the example embodiments included herein, including one of the image sensors shown in FIGS. 2 to 12.

The lens 1010 concentrates incident light on the image sensor 1020. The image sensor 1020 generates RGB data for received light through the lens 1010.

In some embodiments, the image sensor 1020 may interface with the engine unit 1040.

The motor unit 1030 may adjust the focus of the lens 1010 or perform shuttering in response to a control signal received from the engine unit 1040. The engine unit 1040 may control the image sensor 1020 and the motor unit 1030.

The engine unit 1040 may be connected to a host/application 1050 (e.g., a computing device that may include a program storing a program of instructions and a processor configured to execute the program of instructions to implement an application and/or to control one or more of the elements of the digital camera 1000).

Hereinafter, the embodiments are illustrated in more detail with reference to examples. However, these examples are exemplary, and the present disclosure is not limited thereto.

Synthesis of Compounds

Synthesis Example 1

[Chemical Formula 1a]

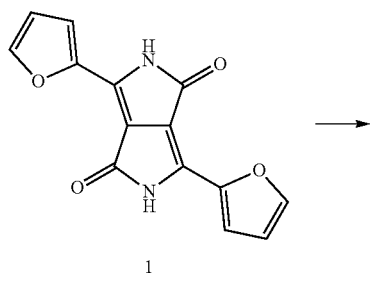

1

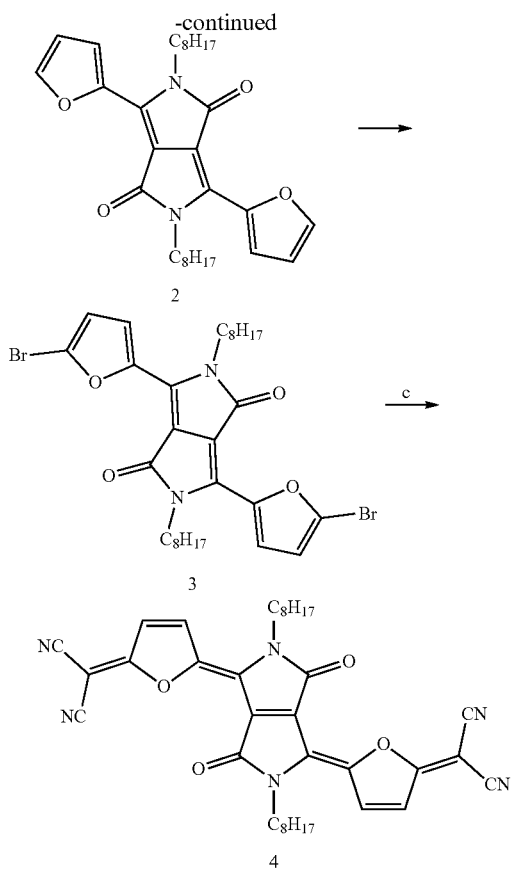

Step 1: 3,6-di(furan-2-yl)-2,5-dihydropyrrolo[3,4-c]pyrrole-1,4-dione

Sodium (4.94 g, 204 mmol) is partitively dissolved in a solution of 2-methyl-2-butanol (500 ml) and $FeCl_3$ (60 mg). When the sodium is completely dissolved, 2-furonitrile (18.9 ml, 204 mmol) is added thereto, the mixture is stirred under argon at 110° C. for 5 minutes, diethyl succinate (10.0 ml, 71.6 mmol) is added thereto in a dropwise fashion, and the obtained mixture is reacted for 4 hours. The reactants are cooled down to 0° C., and acetic acid (30 ml) dissolved in 50 ml of methanol is added thereto. The obtained mixture is reacted for 30 minutes under a reflux condition and cooled down to 0° C., and methanol (300 ml) is additionally added thereto. The obtained dark black/purple precipitate is filtered, washed with methanol and water, and dried under vacuum at 40° C. to obtain a product (15.96 g, 59.5 mmol, a yield of 83%).

Step 2: 3,6-di(furan-2-yl)-2,5-dioctyl-2,5-dihydro-pyrrolo[3,4-c]pyrrole-1,4-dione The degassed solution of Step 1 (3.00 g, 11.18 mmol) and potassium carbonate (6.18 g, 44.74 mmol) are reacted in NMP (200 ml) under argon at 100° C. for 1 hour, and 1-bromooctane (5.80 ml, 33.55 mmol) is added thereto in a dropwise fashion for 20 minutes, and the mixture is reacted at 100° C. for 4 hours. The reactants are cooled down to 0° C., and a precipitate obtained by adding methanol (125 ml) thereto is filtered. The obtained product is recrystallized in ethanol to obtain a dark red needle-type Product 2 (4.46 g, a yield of 81%).

$^1$H NMR (400 MHz, Chloroform-d) δ 8.33 (d, J=3.7 Hz, 2H), 7.66 (d, J=1.8 Hz, 2H), 6.72 (dd, J=3.7, 1.8 Hz, 2H), 4.13 (t, J=7.5 Hz, 4H), 1.72 (pent, J=7.5 Hz, 4H), 1.47. 1.20 (m, 20H), 0.88 (t, J=6.8 Hz, 6H).

Step 3: 3,6-bis(5-bromofuran-2-yl)-2,5-dioctyl-2,5-dihydropyrrolo[3,4-c]pyrrole-1,4-dione NBS (0.42 g, 2.33 mmol) obtained by dissolving Product 2 (0.50 g, 1.02 mmol) in chloroform (20 ml) at room temperature is added thereto, and the obtained mixture is reacted for 2 hours in a dark environment. A precipitate obtained by adding methanol (20 ml) thereto is filtered and recrystallized in chloroform/methanol to obtain a dark red needle-type product (0.41 g, a yield of 62%).

$^1$H NMR (400 MHz, Chloroform-d) δ 8.28 (d, J=3.8 Hz, 2H), 6.66 (d, J=3.7 Hz, 2H), 4.08 (t, J=7.6 Hz, 4H), 1.72 (pent, J=7.3 Hz, 4H), 1.35-1.26 (m, 20H), 0.94-0.86 (m, 6H).

Step 4: 2,2'-((5E,5'E)-(2,5-dioctyl-3,6-dioxo-2,3,5,6-tetrahydropyrrolo[3,4-c]pyrrole-1,4-diylidene)bis(furan-5,2(5H)-diylidene))dimalononitrile Malononitrile (0.255 g 3.86 mmol) dissolved in 10 ml of THF is added to sodium hydride (60% disp, 0.137 g, 3.43 mmol) in 10 ml of THF. The obtained suspension is heated up to 35° C. to obtain a transparent orange/brown solution. The product obtained from Step 3 (0.300 g, 0.343 mmol) and tetrakis(triphenylphosphine)palladium (0) (0.396 g, 0.343 mmol) are dissolved in THF (15 ml) in another flask, degassed, and then, heated and reacted for 1 hour under a reflux condition. Malononitrile and sodium hydride are added to the obtained solution. The reactants are refluxed for 6 hours, cooled to 0° C., and after stopping the reaction with 2 M hydrochloric acid (10 ml), three times extracted with 50 ml of chloroform. The obtained organic material is reacted with 20 ml of sodium hypobromite obtained by stirring saturated bromine water (30 mL) with 10 g of sodium hydroxide dissolved in 25 mL of water at room temperature for 4 hours. The reactants are diluted in 20 ml of water, three times extracted with 50 ml of chloroform, dried with MgSO$_4$, and filtered. The obtained compound is purified with silica column through column chromatography (CHCl$_3$:hexane=2:1) and recrystallized with chloroform and acetonitrile to obtain metallic green polycrystalline powder (60 mg, 71 μmol, a yield of 9%).

$^1$H NMR (400 MHz, Chloroform-d) δ 8.96 (d, J=5.5 Hz, 2H), 7.20 (d, J=5.5 Hz, 2H), 4.14 (t, J=7.5 Hz, 4H), 1.74 (m, 4H), 1.49. 1.42 (m, 4H), 1.40. 1.21 (m, 16H), 0.94. 0.80 (m, 6H). $^{13}$C NMR (101 MHz, Chloroform-d) δ 176.02, 160.36, 144.14, 139.15, 136.16, 123.96, 121.16, 111.81, 110.87, 61.57, 43.69, 31.76, 30.07, 29.34, 29.08, 26.46, 22.61, 14.09. FT-ATR-IR (cm$^{-1}$) 3110 w, 3080 w, 2950 w, 2920 w, 2850 w, 2220 m, 1710 s, 1620 w, 1580 s. HRMS found: 619.3027; C36H39N6O4 (MH$^+$) requires 619.3033.

Figure 14:
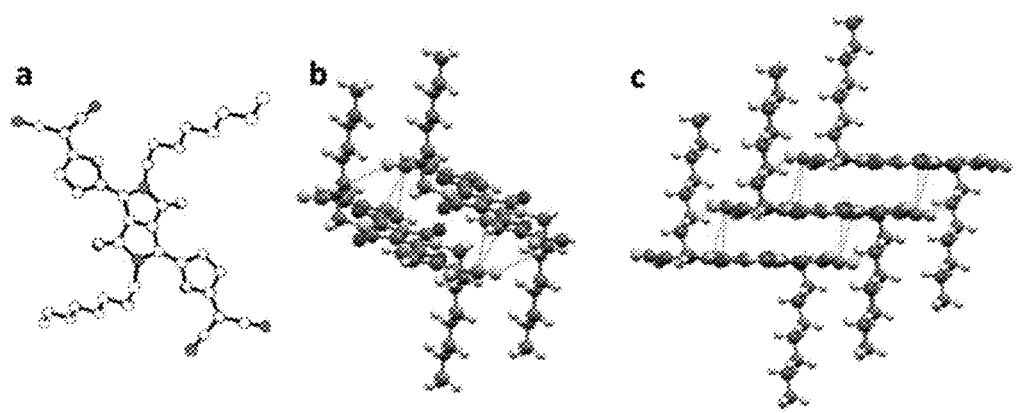
FIG. 14 is a reference view showing a single crystal structure of the compound obtained in Synthesis Example 1.

A monocrystalline structure of the compound obtained from Synthesis Example 1 is shown in FIG. 14.

In FIG. 14, a shows the monocrystalline structure of the compound of Synthesis Example 1, and b and c show a molecular packing of the compound of Synthesis Example 1.

Referring to FIG. 14, the compound of Synthesis Example 1 is expected to have a desirable structure for a charge movement due to formation of a hydrogen bond between oxygen and hydrogen.

Synthesis Example 2

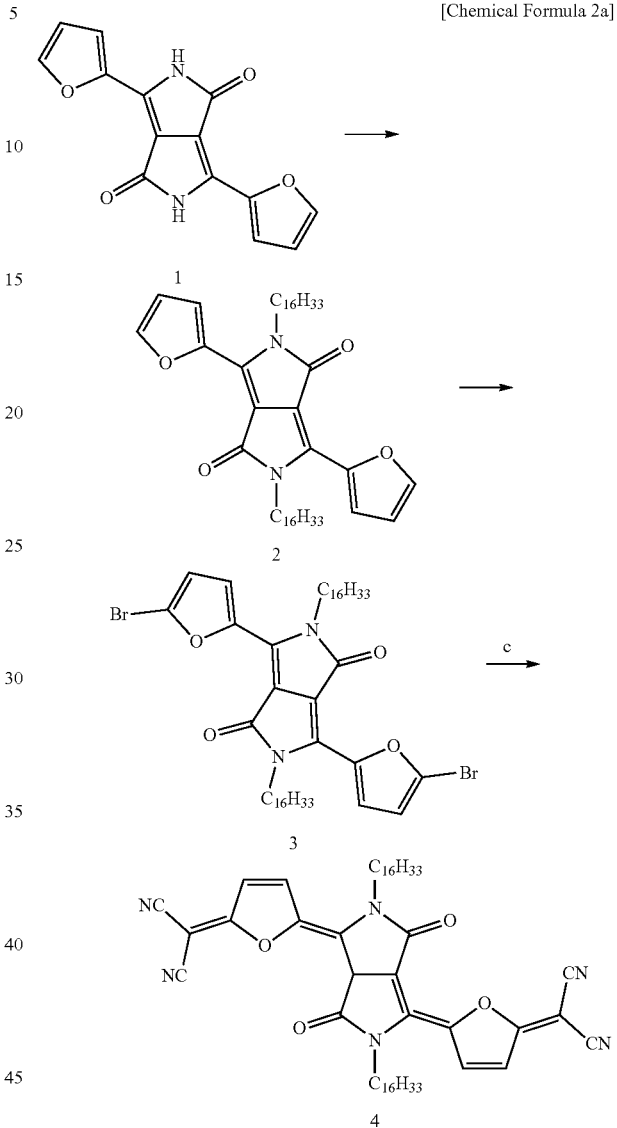

[Chemical Formula 2a]

Step 2: 3,6-di(furan-2-yl)-2,5-dihexadecyl-2,5-dihydropyrrolo[3,4-c]pyrrole-1,4-dione The product 1 obtained from Step 1 of Synthesis Example 1 (4.0 g, 14.9 mmol) and 1-bromohexadecane (13.7 g, 59.7 mmol) are reacted under the same reaction condition as Step 2 of Synthesis Example 1 to obtain dark red powder (9.1 g, a yield of 85%).

$^1$H NMR (400 MHz, Chloroform-d) δ 8.30 (dd, J=3.7, 0.7 Hz, 2H), 7.64 (dd, J=1.7, 0.7 Hz, 2H), 6.70 (dd, J=3.7, 1.7 Hz, 2H), 4.11 (t, J=7.6 Hz, 4H), 1.69 (pent, J=7.5 Hz, 4H), 1.38-1.22 (m, 52H), 0.86 (t, J=6.7 Hz 6H).

Step 3: 3,6-bis(5-bromofuran-2-yl)-2,5-dihexadecyl-2,5-dihydropyrrolo[3,4-c]pyrrole-1,4-dione The product of Step 2 (7.0 g, 9.76 mmol) and NBS (4.0 g, 22.5 mmol) are used under the same condition as Step 3 of Synthesis Example 1 to obtain dark red powder (5.9 g, a yield of 69%). $^1$H NMR (400 MHz, Chloroform-d) δ 8.25 (d, J=3.7 Hz, 2H), 6.63 (d, J=3.7 Hz, 2H), 4.05 (t, J=7.6 Hz, 4H), 1.68 (pent, J=7.6 Hz, 4H), 1.31-1.27 (m, 52H), 0.87 (t, J=6.6 Hz, 6H).

Step 4. 2,2'-((5E,5'E)-(2,5-dihexadecyl-3,6-dioxo-2, 3,5,6-tetrahydropyrrolo[3,4-c]pyrrole-1,4-diylidene) bis(furan-5,2(5H)-diylidene))dimalononitrile The product of Step 3 (0.50 g, 0.572 mmol) and tetrakis(triphenylphosphine)palladium (0) (0.66 g, 0.572 mmol), sodium hydride (0.183 g, 4.57 mmol), and malononitrile (0.38 g, 5.71 mmol) are used under the same method as Step 4 of Synthesis Example 1 to obtain a desired product (67 mg, a yield of 14%). $^1$H NMR (400 MHz, Chloroform-d) δ 8.96 (d, J=5.5 Hz, 2H), 7.20 (d, J=5.5 Hz, 2H), 4.14 (t, J=7.5 Hz, 4H), 1.74 (p, J=7.6 Hz 4H), 1.55-1.20 (m, 52H), 0.94-0.80 (m, 6H). $^{13}$C NMR (101 MHz, Chloroform-d) 175.97, 160.44, 144.23, 139.03, 136.27, 123.91, 121.22, 111.70, 110.79, 61.77, 43.80, 31.94, 30.09, 29.70, 29.65, 29.57, 29.44, 29.39, 29.34, 26.51, 22.67, 14.03. FT-ATR-IR (cm-1) 3110 w, 3080 w, 2950 w, 2920 s, 2850 m, 2220 m, 1710 s, 1620 w, 1570 s. HRMS found: 843.5523; C52H71N6O4 (MH$^+$) requires 843.5537.

Synthesis Example 3

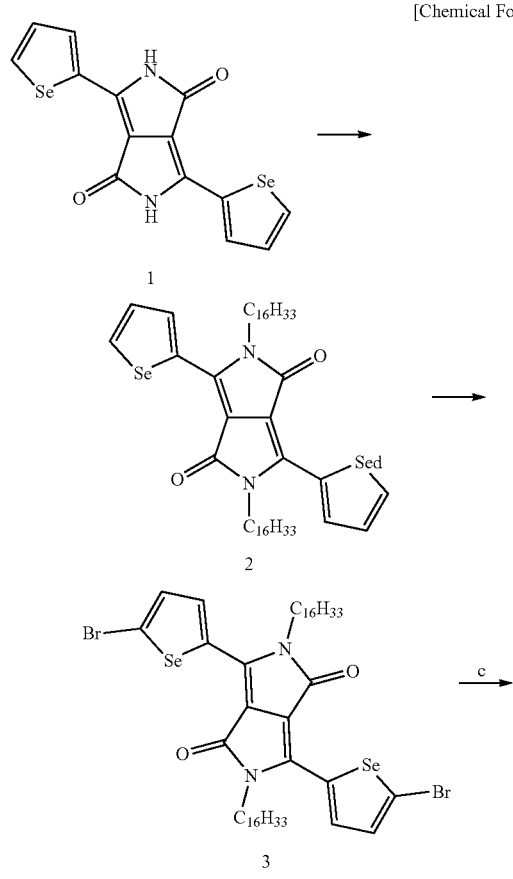

[Chemical Formula 3a]

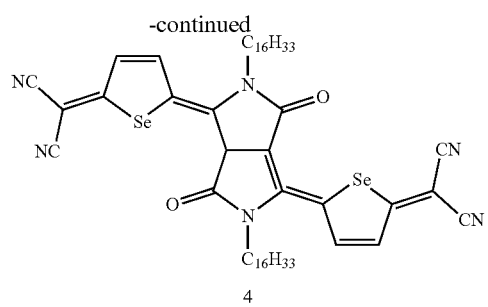

Step 1: 3,6-di(selenophen-2-yl)-2,5-dihydropyrrolo[3,4-c]pyrrole-1,4-dione

Sodium (0.74 g, 32.04 mmol) is several times partitively added to FeCl$_3$ (50 mg) dissolved in 2-methyl-2-butanol (125 ml). When the sodium is dissolved, selenophene-2-carbonitrile (5 g, 32.04 mmol) is added thereto under argon at 110° C., the mixture is stirred for 5 minutes, diethyl succinate (1.8 ml, 10.68 mmol) is added thereto in a dropwise fashion, and the obtained mixture is reacted for 4 hours. The reactants are cooled down, and 5 ml of acetic acid dissolved in 10 ml of methanol is added thereto. Then, the reactants are refluxed for 30 minutes and cooled down to 0° C., and methanol (100 ml) is added thereto. The obtained dark black/purple precipitate is filtered, washed with methanol and water, and vacuum-dried at 40° C. to obtain a product (1.3 g, a yield of 30%).

Step 2: 2,5-dihexadecyl-3,6-di(selenophen-2-yl)-2, 5-dihydropyrrolo[3,4-c]pyrrole-1,4-dione 3,6-di(selenophen-2-yl)-2,5-dihydropyrrolo[3,4-c]pyrrole-1,4-dione (1.00 g 2.54 mmol) and potassium carbonate (1.03 g 7.62 mmol) are dissolved in degassed NMP, and the solution is heated at 100° C. for one hour. 1-bromohexadecane (1.78 ml 5.84 mmol) is added thereto in a dropwise fashion for 20 minutes, and the mixture is stirred at 100° C. for 4 hours. The resultant is cooled down 0° C., methanol (25 ml) is added thereto, and a precipitate produced therein is filtered and recrystallized in hot CHCl$_3$/ethanol to obtain a product (1.08 g, a yield of 51%).

$^1$H NMR (400 MHz, Chloroform-d) δ 8.33 (d, J=3.7 Hz, 2H), 7.66 (d, J=1.8 Hz, 2H), 6.72 (dd, J=3.7, 1.7 Hz, 2H), 4.13 (t, J=7.5 Hz, 4H), 1.72 (p, J=7.5 Hz, 4H), 1.47-1.20 (m, 52H), 0.88 (t, J=6.8 Hz, 6H).

Step 3: 3,6-bis(5-bromoselenophen-2-yl)-2,5-dihexadecyl-2,5-dihydropyrrolo[3,4-c]pyrrole-1,4-dione The product of Step 2 (0.5 g 0.594 mmol) is dissolved in chloroform (40 ml), NBS (0.242 g 1.26 mmol) is added thereto, and the mixture is reacted at room temperature for 2 hours in a dark chamber. Methanol (40 ml) is added thereto, and a precipitate produced therein is filtered and recrystallized from chloroform/methanol to obtain a product (0.243 g, a yield of 40%).

$^1$H NMR (400 MHz, Chloroform-d) δ 8.28 (d, J=3.8 Hz, 2H), 6.66 (d, J=3.7 Hz, 2H), 4.08 (t, J=7.5 Hz, 4H), 1.72 (pent, J=7.3 Hz, 4H), 1.41 (m, 4H), 1.35. 1.26 (m, 48H), 0.94. 0.86 (m, 6H).

Step 4: 2,2'-((5E,5'E)-(2,5-dihexadecyl-3,6-dioxo-2,3,5,6-tetrahydropyrrolo[3,4-c]pyrrole-1,4-diylidene)bis(selenophene-5,2(5H)-diylidene))dimalononitrile Malononitrile (0.198 g 3.00 mmol) dissolved in 15 ml of THF is added to 15 ml of a THF sodium hydride suspension (60% disp., 0.072 g, 1.8 mmol) at 0° C., and the obtained suspension is slowly heated up to 35° C. to obtain a transparent orange/brown solution. In another flask, 3,6-bis (5-bromoselenophen-2-yl)-2,5-dihexadecyl-2,5-dihydropyrrolo[3,4-c]pyrrole-1,4-dione (0.300 g, 0.30 mmol) and tetrakis(triphenylphosphine)palladium (0) (0.347 g, 0.30 mmol) are dissolved in THF (20 ml), the solution is refluxed for 1 hour while degassed and then, four times equally partitively added to the prepared malononitrile and sodium hydride suspension over 90 minutes, and the obtained mixture is refluxed for 16 hours. The resultant is cooled down to 0° C., sodium hypobromite obtained by adding 30 ml of saturated bromine water to 25 ml of a sodium hydroxide (10 g) aqueous solution is added thereto, and the obtained mixture is stirred at RT for 6 hours. The reaction mixture is three times extracted with 50 ml of dichloromethane, and the obtained organic material is washed with salt water, treated with dry $MgSO_4$, and filtered. The obtained compound is separated through silica gel column chromatography by using dichloromethane and recrystallized from a chloroform/acetonitrile solution to obtain a green compound (120 mg, a yield of 41%).

$^1$H NMR (400 MHz, Chloroform-d) δ 9.49 (d, J=6.09 Hz, 2H), 7.42 (d, J=6.16 Hz, 2H), 3.98 (t, J=6.2 Hz, 4H), 1.75 (m, 4H), 1.52-1.21 (m, 52H), 0.88 (m, 6H). $^{13}$C NMR (101 MHz, $CDCl_3$) 175.60, 161.44, 149.27, 135.95, 135.05, 132.73, 130.93, 114.10, 112.08, 75.34, 42.82, 31.93, 30.26, 29.70, 29.65, 29.60, 29.52, 29.41, 29.34, 29.15, 26.84, 22.67, 14.02. FT-ATR-IR ($cm^{-1}$), 3080 vw, 2920 m, 2850 m, 2220 m, 1710 s.

Additional Synthesis Examples 4 to 6

Absorption characteristics and an energy level of the molecules according to Synthesis Examples 4 to 6 are simulated. The simulation is performed a through density function theory (DFT) calculation (B3LYP/6-31 basis set) by using a Gaussian View 5.0.8 software.

Synthesis Example 4

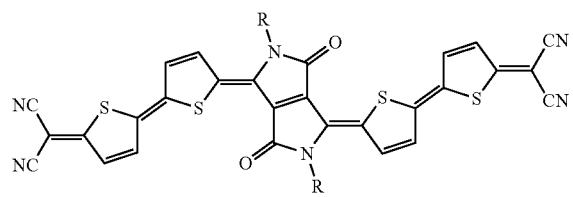

[Chemical Formula 1d]

In Chemical Formula 1d, R=H or alkyl chain (C: 0-16).
λmax, simul: 835 nm

Synthesis Example 5

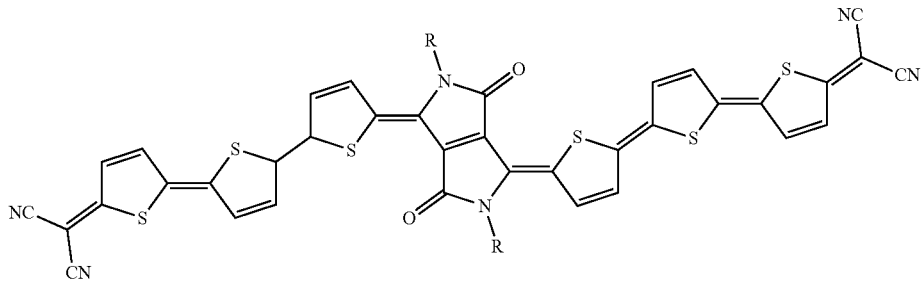

[Chemical Formula 1e]

In Chemical Formula 1e, R=H or alkyl chain (C: 0-16).
λmax, simul: 956 nm

Synthesis Example 6

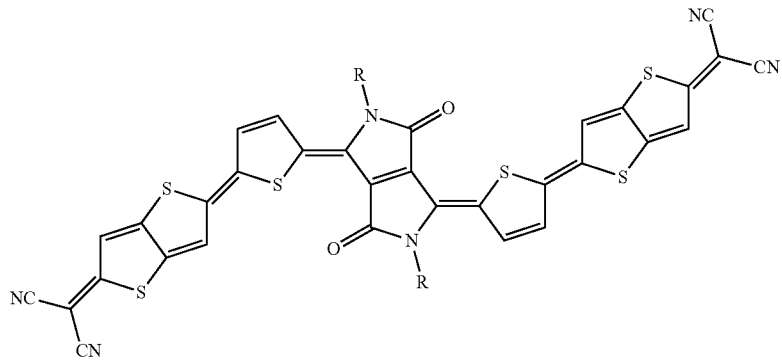

[Chemical Formula 1f]

In Chemical Formula 1f, R=H or alkyl chain (C: 0-16),

λmax, simul: 931 nm

The compounds according to additional Synthesis Examples 4 to 6 in a thin film state show a maximum absorption wavelength in a near infrared region ranging from greater than or equal to 700 nm to less than or equal to 1,000 nm.

Infrared Ray Light Absorption Characteristics

The compounds according to Synthesis Examples 2 to 3 are thermally deposited into 70 nm-thick thin films under high vacuum (<10$^{-7}$ Torr) at a speed of 0.1 to 1.0 Å/s, and a thickness, a refractive index (n), and an extinction coefficient (k) of the thin films are measured by using Variable angle spectroscopy ellipsometry (VASE, J. A. Woollam). A maximum absorption wavelength of the thin films of the compounds according to Synthesis Examples 2 to 3 is measured by using a UV-2450 UV-Visible Spectrophotometer (Shimadzu Corp.).

The results are shown in Table 1.

TABLE 1

|  | DFT HOMO (eV) | DFT LUMO (eV) | TD-DFT $\lambda_{max}$ (gas) (nm) | $\lambda_{max}$ Thin film (nm) | ε (L/mol cm) |
|---|---|---|---|---|---|
| Syn. Ex. 2 | −6.33 | −4.46 | 606 | 732 | 70400 |
| Syn. Ex. 3 | −6.29 | −4.49 | 638 | 721 | 63700 |

Referring to Table 1, the compounds according to Synthesis Examples 2 to 3 have a maximum absorption wavelength in a near-infrared light wavelength of greater than or equal to 700 nm. On the other hand, the compounds according to Synthesis Example 1 and Synthesis Example 2 have a length difference of an alkyl group linked with a nitrogen atom of diketopyrrolopyrrole (DPP) and thus may be expected to have a similar maximum absorption wavelength.

Organic Semiconductor Characteristics

The compounds according to Synthesis Examples 1 to 3 may be used to manufacture each field effect transistor having a top-gate structure, and their transistor characteristics are evaluated. The top gate/bottom contact device is manufactured by using a 40 nm-thick Au source-drain electrode and a CYTOP dielectric on a glass thin film. Herein, a shadow mask is used to deposit Au to be 40 nm thick to form the source-drain electrode on the glass thin film (a channel width: 1000 μm, a channel length; 300 μm). Subsequently, the compounds according to Synthesis Examples 1 to 3 are respectively mixed with poly(α-methyl styrene) (PαMS) in a weight ratio of 1:1 and then, dissolved in hot tetrahydronaphthalene in a concentration of 20 mg/ml and then, spin-coated at a speed of 2000 rpm on the preheated glass thin film. The obtained film is annealed at 160° C. for 1 minute, the CYTOP dielectric is spin-coated, and Au is deposited to manufacture the transistor.

Charge mobility, a threshold voltage, and a current on/off ratio of each organic thin film transistor manufactured by respectively using the compounds according to Synthesis Examples 1 to 3 are shown in Table 2.

TABLE 2

|  | $\mu_{sat}$ ($\mu_{sat\,max}$) (cm$^2$V$^{-1}$S$^{-1}$) | $\mu_{lin}$ (cm$^2$V$^{-1}$S$^{-1}$) | V$_{Th}$ (V) | I$_{on}$/I$_{off}$ |
|---|---|---|---|---|
| Syn. Ex. 1 | 0.050 | 0.031 ± 0.0067 | 19.4 ± 2.9 | 10$^2$-10$^3$ |
| Syn. Ex. 2 | 0.020 | 0.016 ± 0.0019 | −7.3 ± 1.8 | 10-10$^2$ |
| Syn. Ex. 3 | 0.024 | 0.020 | −10.2 | 10-10$^2$ |

In Table 2, $\mu_{sat}$ and $\mu_{lin}$ are calculated from a transfer characteristic graph showing relationship between a gate voltage (V$_G$) and a current. $\mu_{sat}$ is calculated according to Relationship Equation 1 by calculating an area (V$_G$) until a drain current (I$_D$) is saturated from a threshold voltage (V$_{th}$).

$$\mu_{sat} = \frac{2L}{W} \frac{I_{Dlin}}{C_i} \frac{1}{(V_G - V_{th})^2} \frac{1}{(V_G - V_{th})^2} \quad \text{(Relationship Equation 1)}$$

$\mu_{lin}$ is calculated according to Relationship Equation 2 by using a slope in an Ohmic mode wherein the drain current (I$_D$) is linear with V$_G$.

$$\mu_{lin} = \frac{L}{W} \frac{I_{Dlin}}{C_i} \frac{V_D}{(V_G - V_{th})} \quad \text{(Relationship Equation 2)}$$

In Relationship Equation 2, L indicates a channel length, W indicates a channel width, Ci indicates capacitance of a gate insulator per unit area, and V$_{th}$ indicates a threshold voltage.

Referring to Table 2, the organic thin film transistors manufactured by respectively using the compounds according to Synthesis Examples 1 to 3 secure charge mobility of greater than or equal to about 0.020 cm$^2$/Vs and a current on/off ratio of greater than or equal to 10$^2$ and thus excellent characteristics.

While this disclosure has been described in connection with what is presently considered to be practical example embodiments, it is to be understood that the inventive concepts are not limited to the disclosed embodiments, but, on the contrary, is intended to cover various modifications and equivalent arrangements included within the spirit and scope of the appended claims.

DESCRIPTION OF SYMBOLS 10B, 10G, 10R, 10IR: lower electrode
20B, 20G, 20R, 20IR: upper electrode
30B, 30G, 30R: photoactive layer
30IR: infrared light absorption layer (photoactive layer)
110: semiconductor substrate
65: lower insulation layer
85: upper insulation layer
100B: blue photo-sensing device
100G: green photo-sensing device
100R: red photo-sensing device
100IR: infrared light sensing device
200, 300, 400: image sensor

What is claimed is:

1. A compound for an infrared light sensing device, the compound represented by Chemical Formula 1:

[Chemical Formula 1]

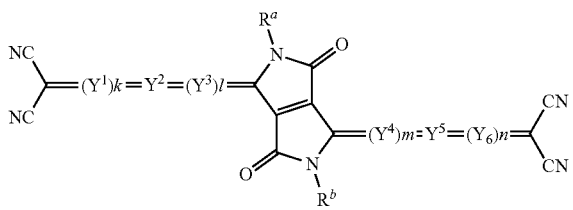

[Chemical Formula 2]

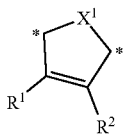

[Chemical Formula 3]

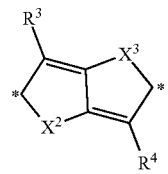

wherein, in Chemical Formula 1,
$Y^1$ to $Y^6$ are independently
a substituted or unsubstituted pentagonal ring including one of O, S, and Se, or
a fused ring of two or more substituted or unsubstituted pentagonal rings including one of O, S, and Se,
k, l, m, and n are independently 0 or 1, and
$R^a$ and $R^b$ are independently hydrogen or a monovalent organic group,
wherein the compound has a maximum absorption wavelength (λmax) in a wavelength range of greater than or equal to about 700 nm and less than or equal to about 1,400 nm in a thin film state, provided that,
when k, l, m, and n are all 0, $Y^2$ and $Y^5$ are independently represented by Chemical Formula 2 or Chemical Formula 3:

wherein, in Chemical Formulae 2 and 3,
$X^1$ is O,
$X^2$ and $X^3$ are independently O or Se,
$R^1$ to $R^4$ are independently hydrogen or a monovalent organic group, and
* is a linking point.

2. The compound of claim 1, wherein, in Chemical Formula 1, $R^a$ and $R^b$ are independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a hydroxy group, a halogen atom, or a combination thereof.

3. The compound of claim 1, wherein the compound is represented by one of Chemical Formulae 4 to 7:

[Chemical Formula 4]

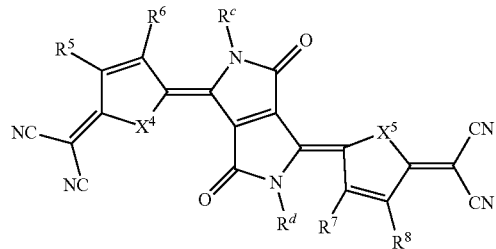

[Chemical Formula 5]

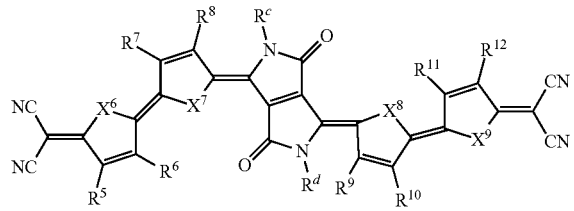

[Chemical Formula 6]

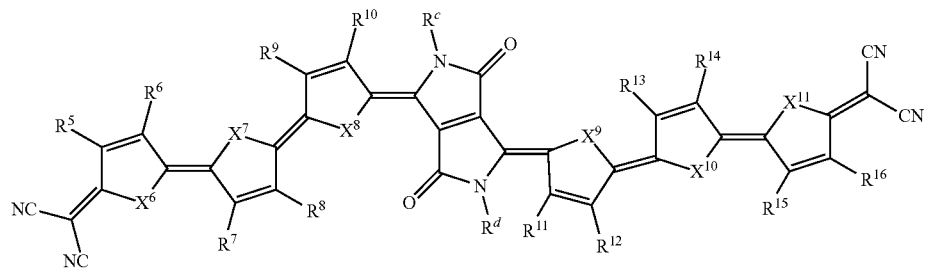

-continued

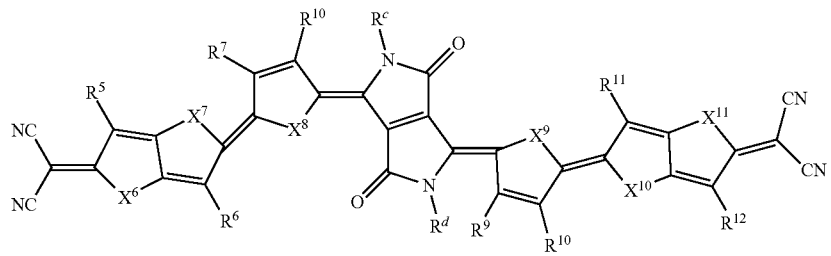

[Chemical Formula 7]

wherein, in Chemical Formulae 4 to 7, $X^4$ and $X^5$ are O, $X^6$ to $X^{11}$ are independently one of O, S, and Se, $R^c$ and $R^d$ are independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a hydroxy group, a halogen atom, or a combination thereof, and $R^5$ to $R^{12}$ are independently hydrogen or a monovalent organic group.

4. The compound of claim 1, wherein the compound is an n-type semiconductor compound.

5. An infrared light sensing device configured to sense light in an infrared wavelength region, the infrared light sensing device comprising:

an upper electrode and a lower electrode facing each other; and an infrared light absorption layer between the upper electrode and the lower electrode, the infrared light absorption layer including a compound represented by Chemical Formula 1:

[Chemical Formula 1]

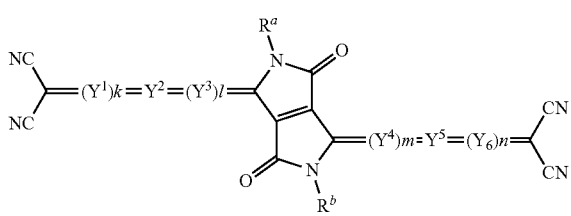

wherein, in Chemical Formula 1, $Y^1$ to $Y^6$ are independently a substituted or unsubstituted pentagonal ring including one of O, S, and Se, or a fused ring of two or more substituted or unsubstituted pentagonal rings including one of O, S, and Se, k, l, m, and n are independently 0 or 1, and $R^a$ and $R^b$ are independently hydrogen or a monovalent organic group, wherein the compound has a maximum absorption wavelength ($\lambda_{max}$) in a wavelength range of greater than or equal to about 700 nm and less than or equal to about 1,400 nm in a thin film state, provided that, when k, l, m, and n are all 0, $Y^2$ and $Y^5$ are independently represented by Chemical Formula 2 or Chemical Formula 3:

[Chemical Formula 2]

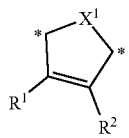

[Chemical Formula 3]

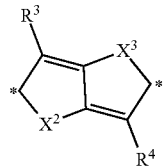

wherein, in Chemical Formulae 2 and 3, $X^1$ is O, $X^2$ and $X^3$ are independently O or Se, $R^1$ to $R^4$ are independently hydrogen or a monovalent organic group, and

* is a linking point.

6. The infrared light sensing device of claim 5, wherein in Chemical Formula 1, $R^a$ and $R^b$ are independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a hydroxy group, a halogen atom, or a combination thereof.

7. The infrared light sensing device of claim 5, wherein the compound is represented by one of Chemical Formulae 4 to 7:

[Chemical Formula 4]

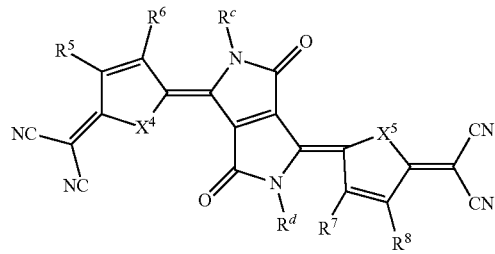

[Chemical Formula 5]

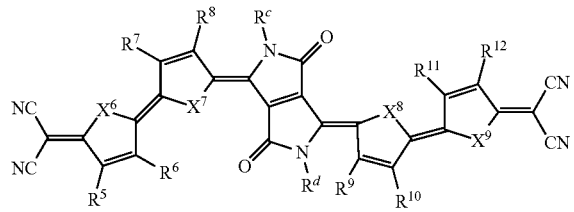

[Chemical Formula 6]

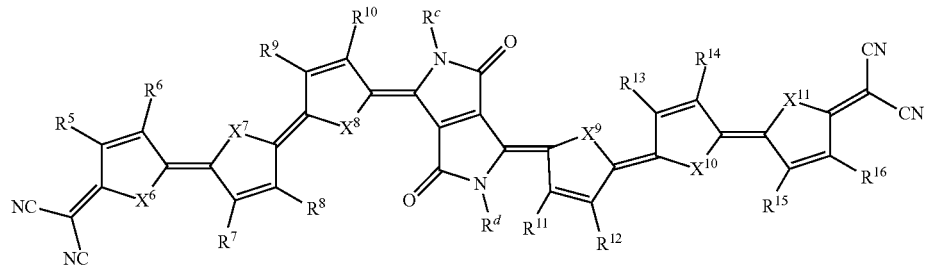

[Chemical Formula 7]

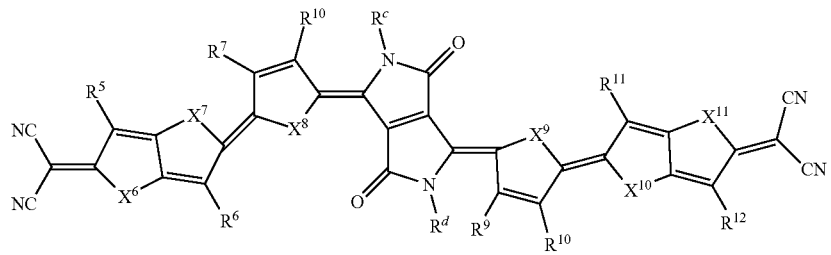

wherein, in Chemical Formulae 4 to 7, $X^4$ and $X^5$ are O, $X^6$ to $X^{11}$ are independently one of O, S, and Se, $R^c$ and $R^d$ are independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a hydroxy group, a halogen atom, or a combination thereof, and $R^5$ to $R^{12}$ are independently hydrogen or a monovalent organic group.

8. The infrared light sensing device of claim 5, wherein the compound is an n-type semiconductor compound.

9. An image sensor, comprising:
the infrared light sensing device of claim 5, and
a visible light sensing device including at least one of a blue photo-sensing device configured to sense light in a blue wavelength region, a red photo-sensing device configured to sense light in a red wavelength region, and a green photo-sensing device configured to sense light in a green wavelength region.

10. The image sensor of claim 9, wherein,
the blue wavelength region is associated with a maximum absorption wavelength ($\lambda_{max}$) of greater than or equal to about 400 nm and less than 500 nm,
the red wavelength region is associated with a maximum absorption wavelength ($\lambda_{max}$) of greater than 580 nm and less than about 700 nm,
the green wavelength region is associated with a maximum absorption wavelength ($\lambda_{max}$) of about 500 nm to about 580 nm, and
the infrared wavelength region has a maximum absorption wavelength ($\lambda_{max}$) of about 700 nm to about 1,400 nm.

11. The image sensor of claim 9, wherein the visible light sensing device and the infrared light sensing device are stacked vertically.

12. The image sensor of claim 9, wherein the visible light sensing device and the infrared light sensing device are in parallel horizontally.

13. An electronic device comprising the image sensor of claim 9.

14. The electronic device of claim 13, wherein the electronic device includes a mobile phone, a digital camera, or a biometric camera.

* * * * *